United States Patent
Bae et al.

(10) Patent No.: US 10,254,165 B2
(45) Date of Patent: Apr. 9, 2019

(54) TIME DIVISION SPREAD SPECTRUM CODE-BASED OPTICAL SPECTROSCOPY SYSTEM CAPABLE OF CONTROLLING IRRADIATION POWER AND METHOD FOR CONTROLLING THE OPTICAL SPECTROSCOPY SYSTEM

(71) Applicant: Korea Advanced Institute of Science and Technology, Daejeon (KR)

(72) Inventors: Hyeon Min Bae, Seoul (KR); Jong Kwan Choi, Daejeon (KR); Min Gyu Choi, Daejeon (KR); Jae Myoung Kim, Daejeon (KR); Gun Pil Hwang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/523,110

(22) PCT Filed: Nov. 14, 2014

(86) PCT No.: PCT/KR2014/010988
§ 371 (c)(1),
(2) Date: Apr. 28, 2017

(87) PCT Pub. No.: WO2016/068377
PCT Pub. Date: May 6, 2016

(65) Prior Publication Data
US 2017/0322083 A1 Nov. 9, 2017

(30) Foreign Application Priority Data
Oct. 30, 2014 (KR) .................. 10-2014-0149065

(51) Int. Cl.
*G01J 3/00* (2006.01)
*G01J 3/28* (2006.01)
(Continued)

(52) U.S. Cl.
CPC .......... *G01J 3/2889* (2013.01); *A61B 5/0059* (2013.01); *A61B 5/0075* (2013.01);
(Continued)

(58) Field of Classification Search
CPC ........ G01J 3/02; G01J 3/00; G01J 3/28; G01J 3/42; G01N 21/359; A61B 5/14;
(Continued)

(56) References Cited

U.S. PATENT DOCUMENTS 6,103,203 A * 8/2000 Fischer ................ A61C 19/004
422/129
2007/0106172 A1 5/2007 Abreu
(Continued)

FOREIGN PATENT DOCUMENTS

JP 2007255918 A 10/2007
JP 2013034901 A 2/2013
(Continued)

OTHER PUBLICATIONS

International Search Report and Written Opinion issued in International Patent Application No. PCT/KR2014/010988, dated Jul. 29, 2015.
(Continued)

*Primary Examiner* — Abdullahi Nur
(74) *Attorney, Agent, or Firm* — Dinsmore & Shohl LLP; Yongsok Choi, Esq.

(57) ABSTRACT

Disclosed are a time division spread spectrum code-based optical spectroscopy system capable of controlling irradiation power and a method for controlling the optical spectroscopy system. The optical spectroscopy system may
(Continued)

comprise: a light transmission unit for irradiating light to a particular region of a subject by means of a light source, wherein the light is irradiated so that the overall energy is consistently maintained by reducing the light irradiation time and increasing the strength of the light; and a light receiving unit for collecting emergent light which has passed through the particular region.

9 Claims, 34 Drawing Sheets

(51) Int. Cl.
*G01N 21/35* (2014.01)
*A61B 5/1455* (2006.01)
*G01J 3/42* (2006.01)
*A61B 5/00* (2006.01)

(52) U.S. Cl.
CPC ............ *A61B 5/14553* (2013.01); *G01J 3/28* (2013.01); *G01J 3/42* (2013.01); *G01N 21/35* (2013.01); *A61B 2562/0238* (2013.01); *A61B 2562/046* (2013.01)

(58) Field of Classification Search
CPC ........... A61B 5/1455; A61B 5/68; A61B 5/00; A61B 5/0022
See application file for complete search history.

(56) References Cited

U.S. PATENT DOCUMENTS

2011/0066014 A1 3/2011 Bechtel et al.
2013/0090541 A1 4/2013 Macfarlane et al.
2013/0256533 A1 10/2013 Bae et al.

FOREIGN PATENT DOCUMENTS

KR 1020140026311 A 3/2014
KR 1020140040813 A 4/2014

OTHER PUBLICATIONS

Serdar Ozturk et al, "A useful algorithm for determining fluence and pulse width for vascular targets using 1,064 nm Nd:YAG laser in an animal model", Lasers in Surgery and Medicine., US, (Jan. 1, 2004), vol. 34, No. 5, Jan. 1, 2017, doi:10.1002/lsm.20059, ISSN 0196-8092, pp. 420-425, XP055472529.
He Liu et al: "The Effect of light conditions on photoplethysmographic Image Acquisition Using a Commercial Camera", IEEE Journal of Translational Engineering in Helth and Medicine, vol. 2, Jan. 1, 2014, pp. 1-11, XP055472101, DOI: 10.1109/JTEHM.2014. 2360200.
R.P. Scott et al, "An eight-user time-slotted SPECTS O-CDMA testbed: demonstration and simulations", Journal of Lightwave Technology., US, (Oct. 1, 2005), vol. 23, No. 10, Oct. 1, 2005, doi:10.1109/JLT.2005.856263, ISSN 0733-8724, pp. 3232-3240, XP055472616.
L. Nguyen, et al., "All-Optical CDMA with bipolar codes", Electronic Letters, (Mar. 16, 1995), pp. 469-470, Mar. 16. 1995, URL: https://www.ece.jhu.edu/~cooper/SPOT/Reference/SPE/All-optical%20CDMA%20with%20bipolar%20codes.pdf, (May 4, 2018), XP055472536.

* cited by examiner

TIME DIVISION SPREAD SPECTRUM CODE-BASED OPTICAL SPECTROSCOPY SYSTEM CAPABLE OF CONTROLLING IRRADIATION POWER AND METHOD FOR CONTROLLING THE OPTICAL SPECTROSCOPY SYSTEM

FIELD OF THE INVENTION

The present invention relates to a time-divided spread spectrum code-based optical spectroscopy system capable of adjusting emission power, and a method for controlling the same.

BACKGROUND

When a living organism attempts to perform a certain action governed by a specific part of a cerebrum, or receives a stimulus associated with the specific part of the cerebrum, neuron cells of the corresponding part of the cerebrum is activated. For example, when perception, calculation, judgment, or the like is carried out, a frontal lobe of the cerebrum and neuron cells corresponding to the frontal lobe are activated. At this time, in the peripheral blood vessels of the activated cells, the concentration of oxyhemoglobin is increased and that of deoxyhemoglobin is reduced in order to supply oxygen to the neuron cells. FIG. 1 shows an example in which the concentration of oxyhemoglobin is increased and that of deoxyhemoglobin is reduced as neuron cells are activated.

Near-infrared spectroscopy (NIRS) can measure the concentration changes of oxyhemoglobin and deoxyhemoglobin caused by the activation of neuronal cells. For example, a human body includes substances called chromophores, which have a chemical structure that can well absorb light of various kinds of specific wavelength bands. Hemoglobin is also a kind of the chromophores, and exhibits a larger degree of absorption than water in a near-infrared region. Since absorption coefficients of oxyhemoglobin and deoxyhemoglobin vary with wavelengths in the near-infrared region, information on the concentration changes of oxyhemoglobin and deoxyhemoglobin in the desired region can be obtained using light of two wavelengths in the near-infrared region.

FIG. 2 shows an example of absorption factors of oxyhemoglobin and deoxyhemoglobin, and FIG. 3 shows an example of a trajectory of light injected into a cerebrum.

First, FIG. 2 shows that the absorption coefficients of oxyhemoglobin (Oxy Hb) and deoxyhemoglobin (Deoxy Hb) are changed according to the wavelengths.

Further, FIG. 3 shows an example of a NIRS system by which light of a near-infrared region is emitted through a source (S) using a laser or a light emitting diode (LED) and the emitted laser or light is detected by a detector (D). Here, the light emitted by the source passes through specific parts of the brain along a curved path as shown in FIG. 3, and the NIRS system can obtain information on the parts of the brain through which the light has passed using information on the light detected by the detector. Background information on the NIRS system is well described in U.S. Patent Application Publication No. 2013/0256533.

SUMMARY OF THE INVENTION

One object of the invention is to provide a mobile and expandable firmware-based optical spectroscopy system and a method for controlling the same.

Another object of the invention is to provide an optical spectroscopy system and a method for controlling the same, by which it is possible to use a pipeline-structured matched filter to implement a matched filter structure for the same time as a bit period of input Walsh codes, and minimize current leakage and nonlinear effects occurring in a switching circuit.

Another object of the invention is to provide an optical spectroscopy system and a method for controlling the same, by which it is possible to use time-divided spread spectrum codes (TDSSC) to reduce duration of 1 of Walsh codes per unit time and inject more intense light, thereby increasing the intensity of the light with the same total energy.

Another object of the invention is to provide an optical spectroscopy system and a method for controlling the same, by which it is possible to modulate light emitted from a plurality of light sources using Walsh codes and emit the modulated light, and detect light coming through a specific region and demodulate the detected light using the Walsh codes, thereby distinguishing the light source that has emitted the light.

Another object of the invention is to provide an optical spectroscopy system and a method for controlling the same, by which it is possible to accumulate input signals using a reference clock used for light emission as a sampling clock, thereby minimizing white Gaussian noise without additional circuitry such as an additional phase locked loop (PLL).

Another object of the invention is to provide an optical spectroscopy system and a method for controlling the same, by which it is possible to process, visualize, and control data in a monitoring device, and guide firmware update according to the release of a new version of firmware included in an attachment device such as a headset.

Another object of the invention is to provide an optical spectroscopy system and a method for controlling the same, by which it is possible to collect, manage, and analyze data measured through a web server and provide personalized results through a monitoring device.

There is provided an optical spectroscopy system, comprising: a light transmission unit for emitting light to a specific region of a subject through a light source, such that total energy is maintained constant by decreasing time of emitting the light and increasing an intensity of the light; and a light reception unit for collecting light coming through the specific region.

According to one aspect of the invention, the light transmission unit decreases an on/off duty ratio of the light emission by a predetermined ratio using time-divided spread spectrum codes (TDSSC), and increases the intensity of the light by the predetermined ratio.

According to another aspect of the invention, the light source comprises a dual wavelength laser device and a dual wavelength light emitting diode (LED) device, and further comprises a level shifter for changing a control voltage domain of a circuit including the laser device and the LED device.

According to another aspect of the invention, when initial power is supplied, a start-up circuit for allocating basic voltage to devices included in the level shifter is connected to both ends of the level shifter.

According to another aspect of the invention, a signal is boosted through the level shifter, the signal corresponding to a code to be used among a predetermined number of mutually independent Walsh codes generated based on a reference clock, and the boosted signal is received in the laser device as an input signal, so that on/off of the input signal is adjusted using a duty control signal applied from a microcontroller unit (MCU).

There is provided a method for controlling an optical spectroscopy system, comprising the steps of: by a light transmission unit included in the optical spectroscopy system, emitting light to a specific region of a subject through a light source, such that total energy is maintained constant by decreasing time of emitting the light and increasing an intensity of the light; and by a light reception unit included in the optical spectroscopy system, collecting light coming through the specific region.

According to the invention, it is possible to provide a mobile and expandable firmware-based optical spectroscopy system and a method for controlling the same.

According to the invention, it is possible to use a pipeline-structured matched filter to implement a matched filter structure for the same time as a bit period of input Walsh codes, and minimize current leakage and nonlinear effects occurring in a switching circuit.

According to the invention, it is possible to use time-divided spread spectrum codes (TDSSC) to reduce duration of 1 of Walsh codes per unit time and inject more intense light, thereby increasing the intensity of the light with the same total energy.

According to the invention, it is possible to modulate light emitted from a plurality of light sources using Walsh codes and emit the modulated light, and detect light coming through a specific region and demodulate the detected light using the Walsh codes, thereby distinguishing the light source that has emitted the light.

According to the invention, it is possible to accumulate input signals using a reference clock used for light emission as a sampling clock, thereby minimizing white Gaussian noise without additional circuitry such as an additional phase locked loop (PLL).

According to the invention, it is possible to process, visualize, and control data in a monitoring device, and guide firmware update according to the release of a new version of firmware included in an attachment device such as a headset.

According to the invention, it is possible to collect, manage, and analyze data measured through a web server and provide personalized results through a monitoring device.

DETAILED DESCRIPTION OF THE PREFERRED EMBODIMENTS

Hereinafter, embodiments of the present invention will be described in detail with reference to the accompanying drawings.

Mobile and Expandable Firmware-Based Optical Spectroscopy System

Figure 1:
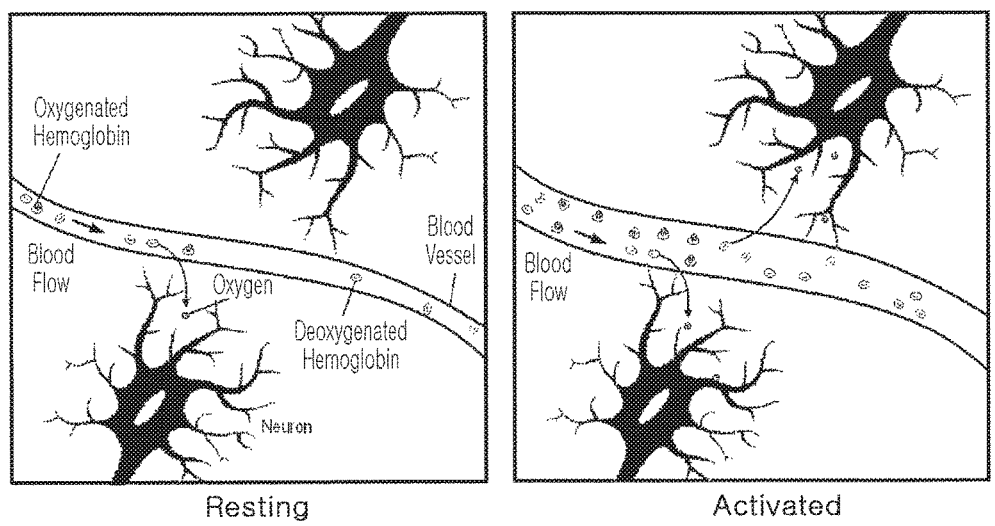
FIG. 1 shows an example in which the concentration of oxyhemoglobin is increased and that of deoxyhemoglobin is reduced as neuron cells are activated.
Figure 2:
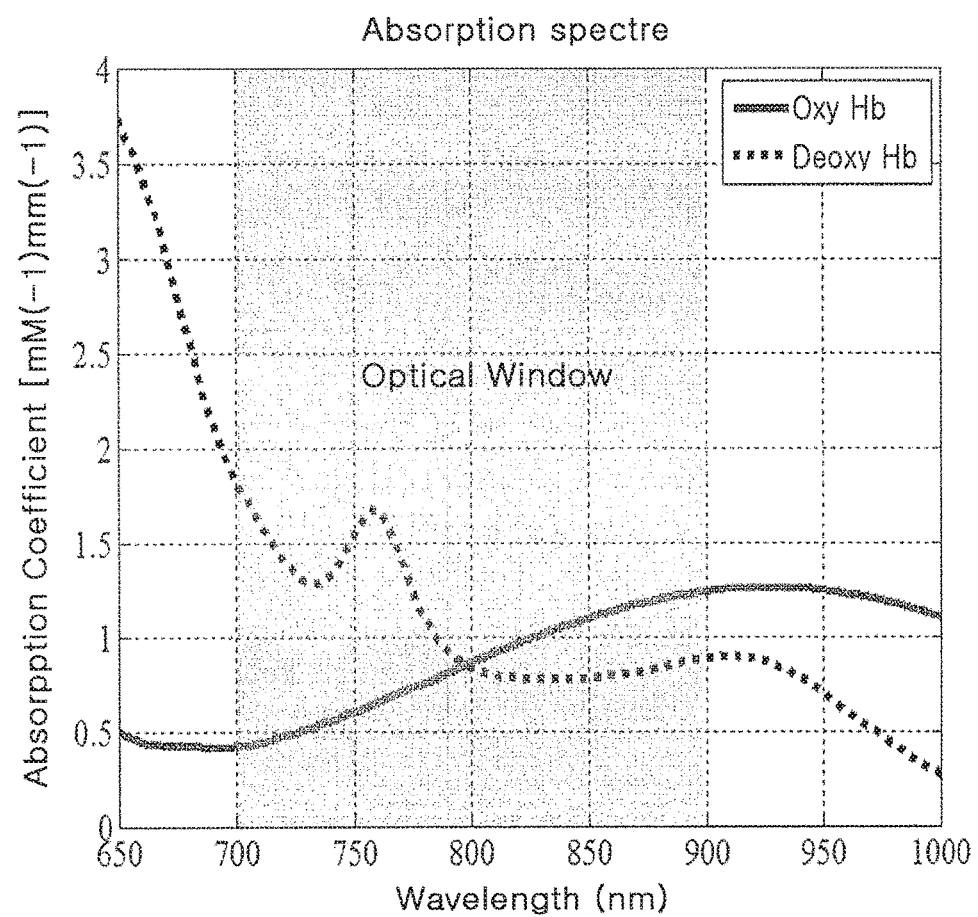
FIG. 2 shows an example of absorption factors of oxyhemoglobin and deoxyhemoglobin.
Figure 3:
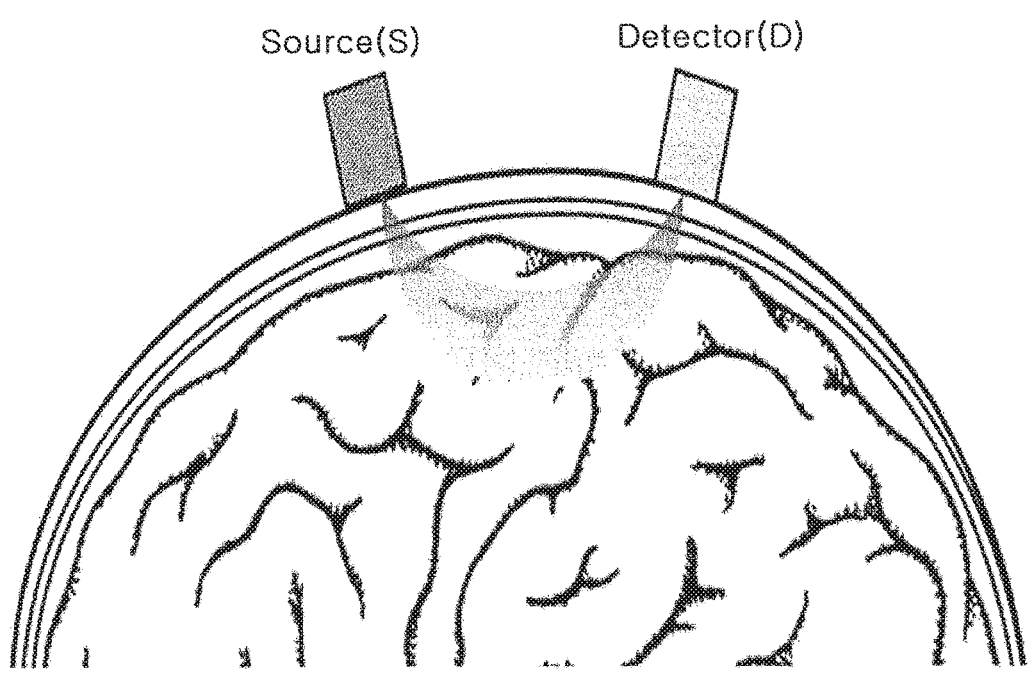
FIG. 3 shows an example of a trajectory of light injected into a cerebrum.
Figure 4:
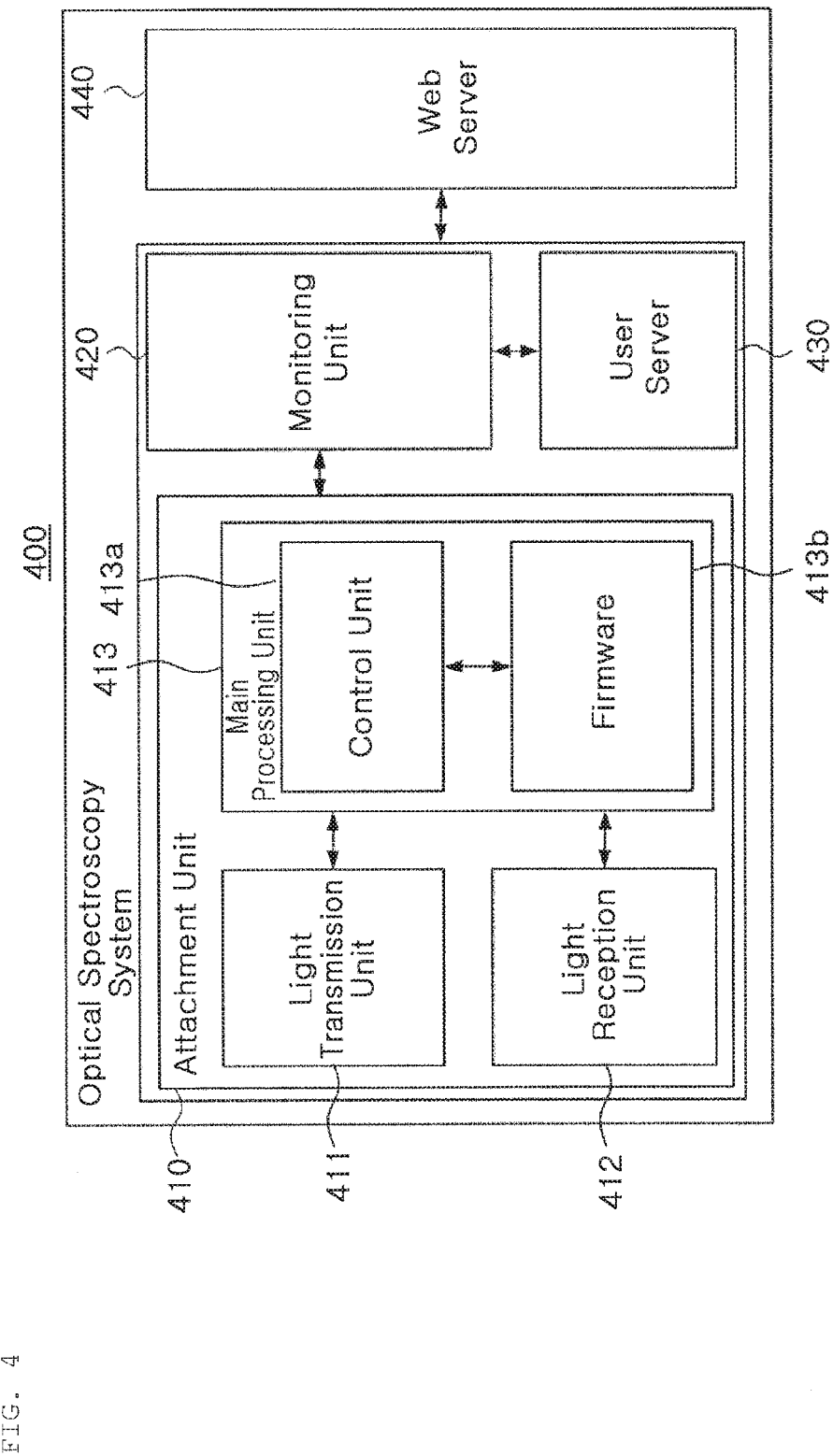
FIG. 4 is a block diagram showing an example of an optical spectroscopy system according to one embodiment of the invention.

FIG. 4 is a block diagram showing an example of an optical spectroscopy system according to one embodiment of the invention.

As shown in FIG. 4, an optical spectroscopy system 400 may comprise an attachment unit 410, a monitoring unit 420, a user server 430, and a web server 440. Here, there may be a plurality of systems each comprising the attachment unit 410, the monitoring unit 420, and the user server 430, and each of the plurality of systems may be implemented to communicate with the web server 440 and receive services from the web server 440. For example, the optical spectroscopy system 400 may be implemented such that a first system comprising a first attachment unit, a first monitoring unit, and a first user server, and a second system comprising a second attachment unit, a second monitoring unit, and a second user server communicate with the web server 440, respectively, or such that three or more systems communicate with the web server 440, respectively. According to another embodiment of the invention, the optical spectroscopy system 400 may also be implemented to comprise only the attachment unit 410, the monitoring unit 420, and the user server 430. The attachment unit 410, the monitoring unit 420, the user server 430, and the web server 440 may be connected to each other through a wired or wireless network to transmit and receive data.

The attachment unit 410 may be implemented in the form of a device attached to a specific part of a user (e.g., an upper end of the user's head). For example, the attachment unit 410 may be implemented in the form of a headset and worn on a region of the user's head to be measured. The attachment unit 410 may comprise a light transmission unit 411, a light reception unit 412, and a main processing unit 413. As shown in FIG. 4, the main processing unit 413 may comprise a control unit 413a and a firmware 413b.

The light transmission unit 411 may comprise at least one module composed of a circuit that actually produces light. For example, the light transmission unit 411 may comprise one or more modules (e.g., a light transmission module 500 to be described below with reference to FIG. 5) implemented to include a laser, or configured to include a light emitting diode (LED) and a LED drive circuit.

The light transmission unit 411 may use multi-wavelength light in a band of wavelengths from 600 nm to 1300 nm, and may comprise a plurality of light sources that emit the multi-wavelength light. Here, the intensity of the light emitted from the light transmission unit 411 may be changed by the monitoring unit 430. Further, the intensity of the light emitted from the light transmission unit 411 may be changed according to a change in the magnitude of current inputted to the laser or the LED, a change in the frequency of light injected into a living organism for a predetermined period of time, or the like.

Figure 5:
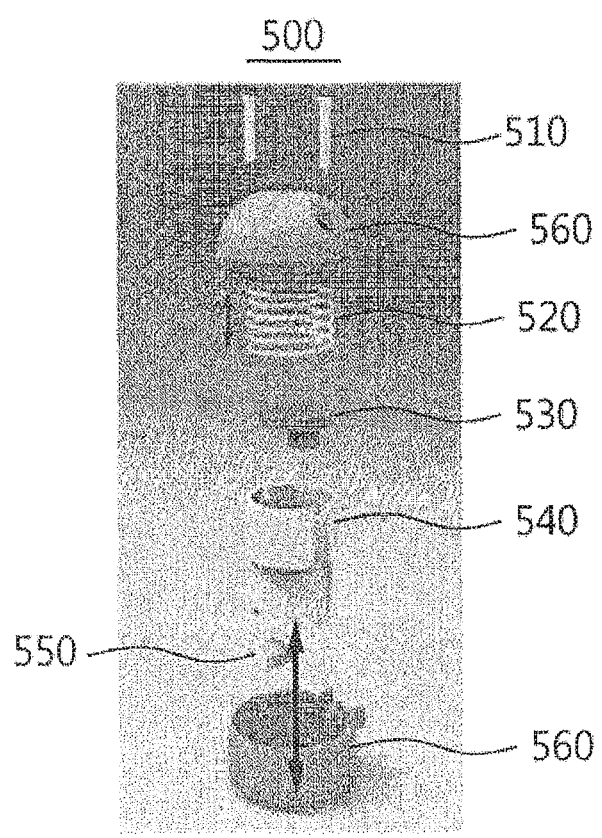
FIG. 5 shows an implementation example of a module constituting a light transmission unit according to one embodiment of the invention.

FIG. 5 shows an implementation example of a module constituting a light transmission unit according to one embodiment of the invention. The light transmission unit according to the present embodiment may correspond to the light transmission unit 411 described with reference to FIG. 4.

A light transmission module 500 may correspond to a light source included in the light transmission unit 411 to emit light. As shown in FIG. 5, the light transmission module 500 may comprise a bolt 510, a spring 520, a light source 530, a cylinder 540, a reference light reception unit 550, and a case 560.

The light source 530 may be implemented in the form of a laser, a LED or the like disposed on a PCB, and inserted in the cylinder 540. The reference light reception unit 550 may be coupled to a side surface of the cylinder to detect light received through a head surface of a user. The light detected by the reference light reception unit 550 may also be used to measure a biological change of the user.

The spring 520, the light source 530, the cylinder 540, and the reference light reception unit 550 may be disposed within the case 560. The case 560 may be implemented such that the top and bottom thereof are coupled to each other through the bolt 510.

The cylinder 540 may be structured such that it is pushed by the spring 520 in a downward direction in FIG. 5. When a subject wears a product like the attachment unit 410 on his/her head, the spring 520 may be used to prevent widening of the gap between the light transmission unit 411 and the subject. For example, the cylinder 540 or the reference light reception unit 550 may be brought into close contact with a measured region of the subject by the force of the spring 520, regardless of the shape or curvature of the measured region of the subject.

The above configuration enables consistent measurements because light can be emitted to the subject while the close contact is constantly maintained, regardless of the state of the measured region of the subject, the gap between the measured region and the attachment unit 410 (such as a headset), or the like. Further, it is possible to decrease the influence of a movement of the subject or a minute movement of the attachment unit 410 on the light transmission, and to reduce the outward leakage of the emitted light.

Referring again to FIG. 4, the light reception unit 412 may comprise at least one module (e.g., a light detection module 600 to be described below with reference to FIG. 6) composed of a photo detector (PD) for collecting light emitted from the light transmission unit 411 and coming through the living organism, and a circuit for driving the photo detector. The light emitted from the light transmission unit 411 may be light modulated with specific codes such as time-divided spread spectrum codes (TDSSC). Here, when light from a plurality of light transmission modules is received by each module of the light reception unit 412, the overlapped form of the TDSSC of the received light may be diverse. The received light may be amplified through a plurality of steps, and the intensity of the received light is diversified according to various conditions when the light is received. Thus, the light reception unit 412 may have a variety of adjustable gains.

Figure 6:
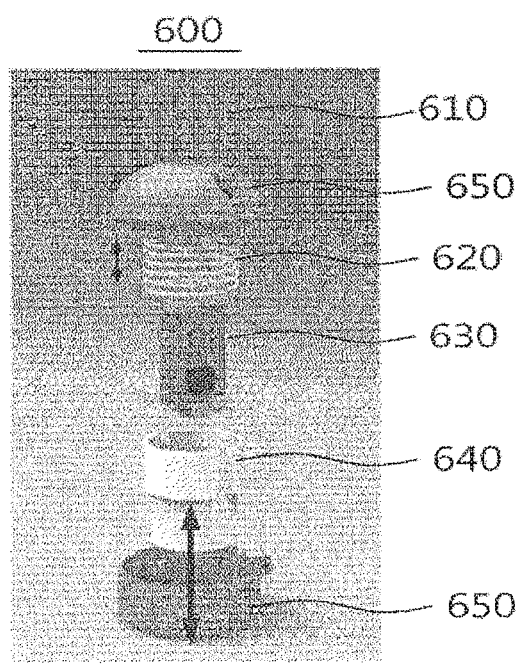
FIG. 6 shows an implementation example of a module constituting a light reception unit according to one embodiment of the invention.

FIG. 6 shows an implementation example of a module constituting a light reception unit according to one embodiment of the invention. The light reception unit according to the present embodiment may correspond to the light reception unit 412 described with reference to FIG. 4.

The light reception module 600 may be a module included in the light reception unit 412 to receive light. As shown in FIG. 6, the light reception module 600 may comprise a bolt 610, a spring 620, a detector 630, a cylinder 640, and a case 650.

The detector 630 may comprise a trans-impedance amplifier (TIA) and a photo detector (PD), and may be disposed within the cylinder 640. The case 650 may contain the spring 620, the detector 630, and the cylinder 640. The case 650 may be implemented such that the top and bottom thereof are coupled to each other through the bolt 610.

The spring 620 may be included to push the cylinder 640 including the detector 630 in a downward direction in FIG. 6. Similar to FIG. 5, the spring 620 may be used to bring the light reception unit 412 into close contact with a measured region of a subject.

Light emitted by the light transmission unit 411 may be received by the detector 630 and converted into an electrical signal. The electrical signal is a signal amplified in a fully differential manner by the TIA included in the detector 630, and the signal outputted from the light reception unit 412 may be inputted to the main processing unit 413 included in the attachment unit 410.

The embodiments of FIGS. 5 and 6 are only intended to facilitate understanding of the invention, and the modules included in the light transmission unit 411 or the light reception unit 412 are not limited to the embodiments of FIG. 5 or 6.

Referring again to FIG. 4, the main processing unit 413 may comprise the control unit 413a and the firmware 413b. The firmware 413b included in the main processing unit 413 may provide the following functions (1) to (4):

(1) a function for appropriately controlling operations of the hardware included in the attachment unit 410 (e.g., controlling the light transmission unit 411, the light reception unit 412, and the main processing unit 413);

(2) a function for separating output data of an A/D converter on a Rx side included in the control unit 413a into optical data of each channel;

(3) a function for transmitting the separated optical data to the monitoring unit 420 using wireless communication (e.g., Bluetooth or Wi-Fi); and (4) a function for providing a firmware update mode and a firmware execution mode through a customized boot loader, and allowing a user to select either the firmware update mode or the firmware execution mode through the user server 430.

The user server 430 may be a device of a user (e.g., an experimenter) for collecting and managing data, managing user information, and transmitting the data to the web server 440 upon obtaining a subject's consent for information provision.

The attachment unit 410 according to the present embodiment may provide the above-described functions (1) to (4) through the firmware 413b, thereby achieving the following two effects:

Firstly, when the hardware configuration of the attachment unit 410 such as a headset is fixed, the firmware 413b may be updated or changed so that newly improved functions are instantly added and used in the main processing unit 413, or the functions of the main processing unit 413 are instantly changed and used, without changing the elements, structure, or the like of the hardware.

Secondly, when the hardware configuration of the attachment unit 410 such as a headset may be expanded, the firmware may be updated or changed to control the expanded hardware configuration, without having to add a special circuit or hardware for driving the light transmission unit 411 or the light reception unit 412, or change the circuit or hardware. Accordingly, the attachment unit 410 may be variably and freely implemented in diverse structures, without being limited to the type of hardware.

Figure 7:
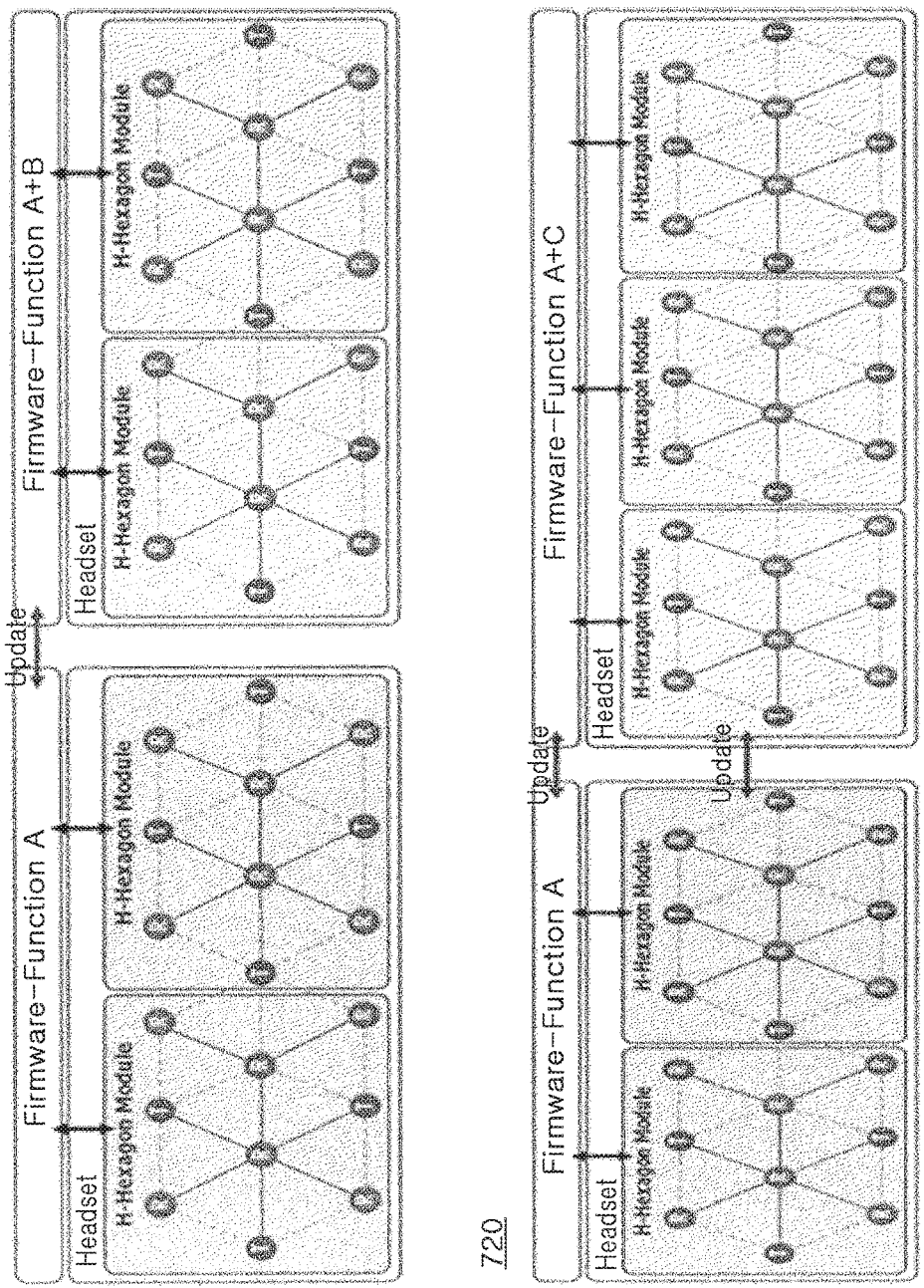
FIG. 7 shows examples of updating firmware with respect to fixed hardware to add a new function, and updating firmware to control expanded hardware according to one embodiment of the invention.

FIG. 7 shows examples of updating firmware with respect to fixed hardware to add a new function, and updating firmware to control expanded hardware according to one embodiment of the invention. The firmware according to the present embodiment may correspond to the firmware 413b described with reference to FIG. 4.

In FIG. 7, T and R may denote a light transmission module and a light reception module, respectively. For example, a first configuration 710 of FIG. 7 shows a headset structure that is fixedly configured to have a H-hexagonal structure (HHS) as a basic structure, by means of seven light transmission modules and twelve light reception modules. Further, a second configuration 720 of FIG. 7 shows an example in which the headset structure is expanded to have ten light transmission modules and eighteen light reception modules.

Here, the firmware (e.g., the firmware 413b) may be updated to add a newly improved function or to change an existing function, even in a fixed state without changing the hardware configuration as in the first configuration 710. The first configuration 710 shows an example in which the firmware having a function A is updated to the firmware having a function A+B.

The second configuration 720 corresponds to an embodiment in which the hardware configuration of the headset is changed/expanded, and shows an example in which the firmware having a function A is updated to the firmware having a function A+C according to the expansion of the hardware.

Further, as described above, the light reception unit 412 may have various adjustable gains. Here, the function for adjusting the gains may be included in the firmware 413b or the monitoring unit 420.

Figure 8:
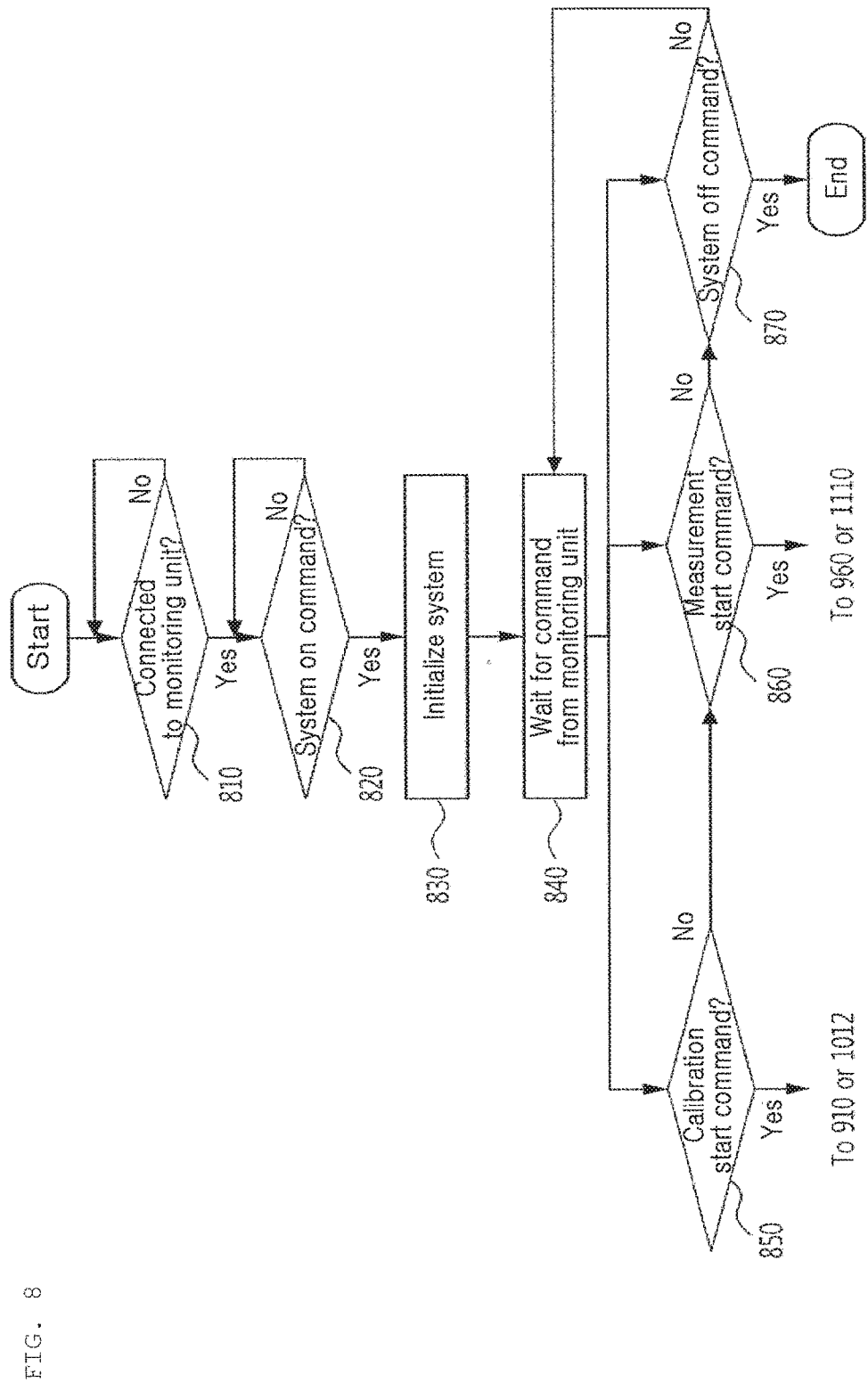
FIG. 8 is a flowchart showing a part of a method for controlling an attachment unit according to one embodiment of the invention.

FIG. 8 is a flowchart showing a part of a method for controlling an attachment unit according to one embodiment of the invention. The attachment unit according to the present embodiment may correspond to the attachment unit 410 described with reference to FIG. 4. Here, the attachment unit 410 may perform steps 810 to 870 under the control of the firmware 413b.

In step 810, the attachment unit 410 may determine whether it is connected to the monitoring unit 420. Here, when the attachment unit 410 is connected to the monitoring part 420, it may perform step 820.

In step 820, the attachment unit 410 may determine whether a system on command is received. For example, the attachment unit 410 may perform step 830 when the system on command is received.

In step 830, the attachment unit 410 may initialize the system. Here, the system may be the attachment unit 410, or the optical spectroscopy system 400 described with reference to FIG. 4.

In step 840, the attachment unit 410 may wait for a command from the monitoring unit 420.

Steps 850, 860 and 870 may indicate that the attachment unit 410 may perform different operations according to commands from monitoring unit 420. For example, in step 870, the attachment unit 410 may determine whether a system off command is received, and may be terminated when the system off command is received. In other words, the method for controlling the attachment unit 410 according to the present embodiment may be terminated according to the system off command from the monitoring unit 420.

In step 850, the attachment unit 410 may determine whether a calibration start command is received. Here, when the calibration start command is received, the attachment unit 410 may perform step 910 of FIG. 9 or step 1012 of FIG. 10. Step 910 may be performed when the function of determining how to adjust the separation and gain of a channel is not included in the firmware 413b but in the monitoring unit 420. Further, step 1012 may be performed when the function of determining how to adjust the separation and gain of a channel is not included in the monitoring unit 420 but in the firmware 413b.

In step 860, the attachment unit 410 may determine whether a measurement start command is received. Here, when the measurement start command is received, the attachment unit 410 may perform step 960 of FIG. 9 or step 1110 of FIG. 11. Step 960 may be performed when the function of determining how to adjust the separation and gain of a channel is not included in the firmware 413b but in the monitoring unit 420. Further, step 1110 may be performed when the function of determining how to adjust the separation and gain of a channel is not included in the monitoring unit 420 but in the firmware 413b.

Figure 9:
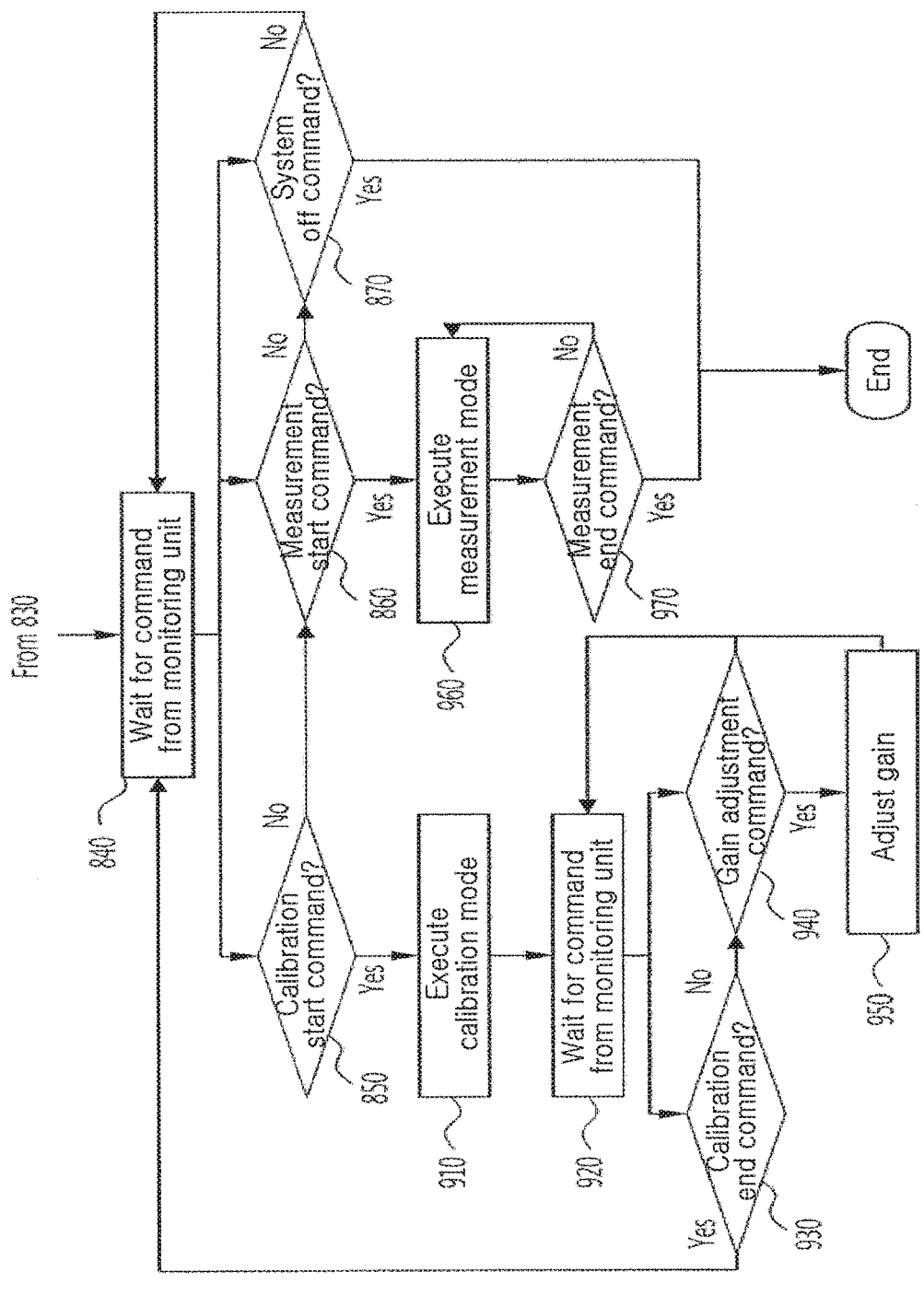
FIG. 9 is a flow chart showing the remaining part of the method for controlling the attachment unit according to one embodiment of the invention.

FIG. 9 is a flow chart showing the remaining part of the method for controlling the attachment unit according to one embodiment of the invention.

When the calibration start command is received in step 850, the attachment unit 410 may execute a calibration mode in step 910 and wait for a command from the monitoring unit 420 in step 920.

Here, when a calibration end command is received in step 930, the attachment unit 410 may return to step 840 and wait for a command from the monitoring unit 420. Further, when a gain adjustment command is received in step 940, the attachment unit 410 may adjust the gain in step 950. Here, the gain adjustment command may include a command to increase or decrease the gain, and the attachment unit 410 may increase or decrease the gain according to the gain adjustment command.

When the measurement start command is received in step 860, the attachment unit 410 may execute a measurement mode in step 960. For example, the attachment unit 410 may emit light of a near-infrared region using a laser or a light emitting diode (LED) through a source (S) included in the light transmission unit 411, and detect the emitted laser or light through a detector (D) included in the light reception unit 412.

When a measurement end command is received in step 970, the attachment unit 410 may terminate the control method. In step 870, the attachment unit 410 may also terminate the control method according to the system off command.

Figure 10:
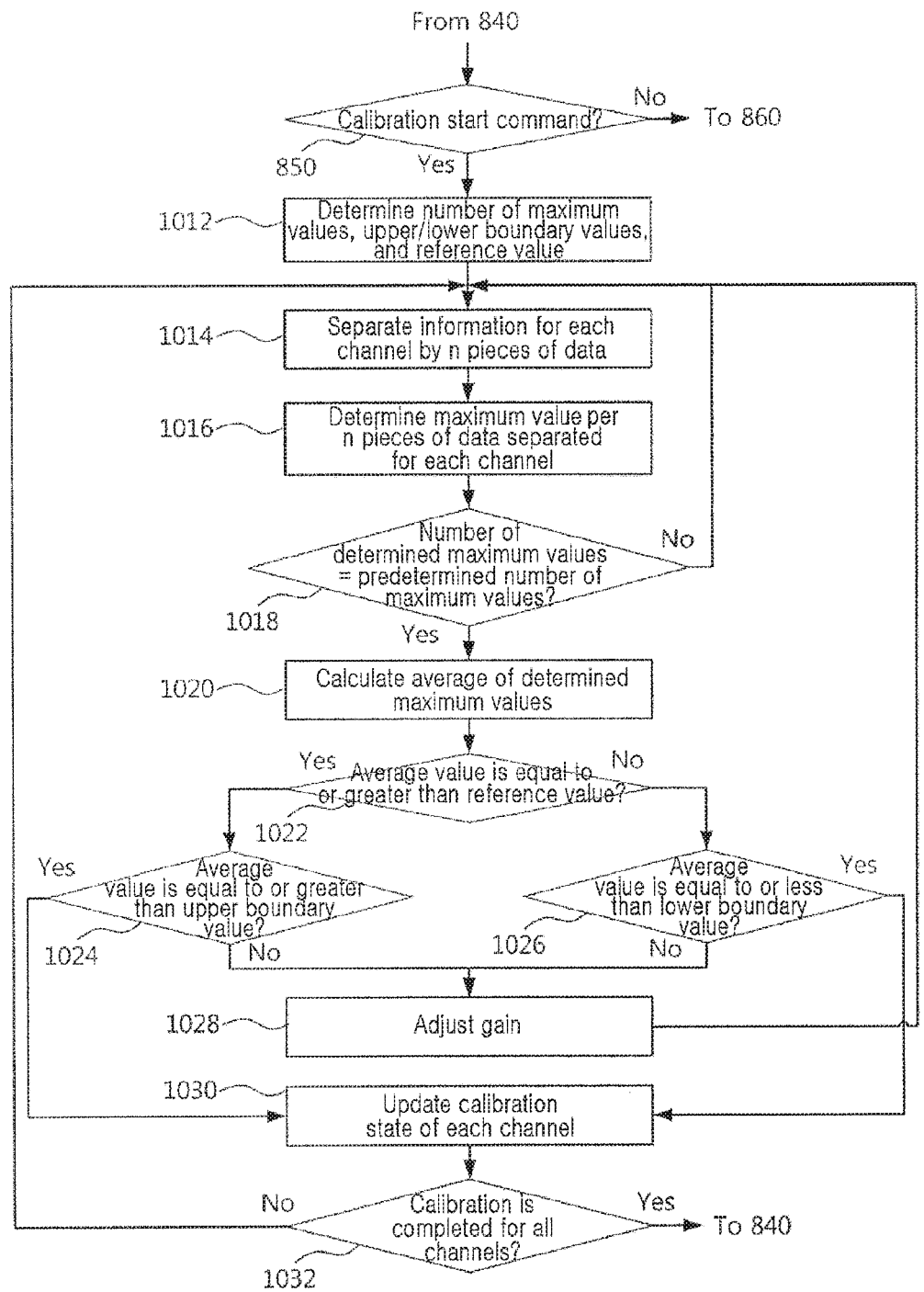
FIGS. 10 and 11 are flowcharts showing the control method for the case where firmware includes a function of determining how to adjust the separation and gain of a channel according to one embodiment of the invention.
Figure 11:
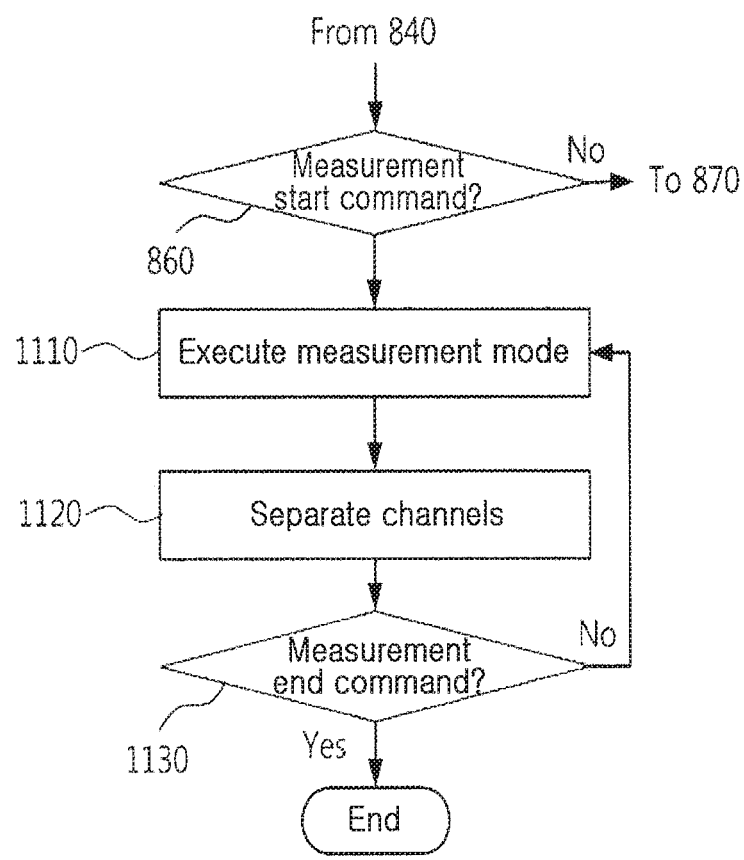

FIGS. 10 and 11 are flowcharts showing the control method for the case where firmware includes a function of determining how to adjust the separation and gain of a channel according to one embodiment of the invention.

First, FIG. 10 shows a process in which the attachment unit 410 adjusts the gain of each channel under the control of the firmware 413b according to the calibration start command in step 850.

In step 1012, the attachment unit 410 may determine the number of maximum values, upper/lower boundary values, and a reference value.

In step 1014, the attachment unit 410 may separate information for each channel by n pieces of data. For example, the attachment unit 410 may separate the channel information by 16 pieces of data.

In step 1016, the attachment unit 410 may determine a maximum value per n pieces of data separated for each channel.

In step 1018, the attachment unit 410 may determine whether the number of the determined maximum values is equal to a predetermined number of maximum values. For example, the attachment unit 410 may separate the channel information by 16 pieces of data to determine the predetermined number of maximum values.

In step 1020, the attachment unit 410 may calculate an average of the determined maximum values.

In step 1022, the attachment unit 410 may determine whether the average value (i.e., the average of the maximum values) is equal to or greater than the reference value. The attachment unit 410 may perform step 1024 when the average value is equal to or greater than the reference value, and perform step 1026 when the average value is less than the reference value.

In step 1024, the attachment unit 410 may perform step 1030 when the average value is equal to or greater than the upper boundary value, and perform step 1028 when the average value is less than the upper boundary value.

In step 1026, the attachment unit 410 may perform step 1030 when the average value is equal to or less than the lower boundary value, and perform step 1028 when the average value is greater than the lower boundary value.

In step 1028, the attachment unit 410 may adjust the gain. For example, the attachment unit 410 may decrease the gain when the average value is equal to or greater than the reference value and less than the upper boundary value. Further, the attachment unit 410 may increase the gain when the average value is less than the reference value and greater than the lower boundary value. After adjusting the gain, the attachment unit 410 may perform step 1014 again.

In step 1030, the attachment unit 410 may update the calibration state of each channel. For example, the attachment unit 410 may update the calibration state of each channel when the average value is equal to or greater than the reference value and equal to or greater than the upper boundary value, or when the average value is less than the reference value and equal to or less than the lower boundary value.

In step 1032, the attachment unit 410 may return to step 840 and wait for a command from the monitoring unit 420 when the calibration is completed for all channels. When the calibration is not completed for all channels, step 1014 may be performed.

Referring to FIG. 11, the attachment unit 410 may execute the measurement mode in step 1110 upon receipt of the measurement start command in step 860, and separate the channels in step 1120. In step 1130, the attachment unit 410 may terminate the control method upon receipt of the measurement end command, or perform step 1110 again to execute the measurement mode.

Figure 12:
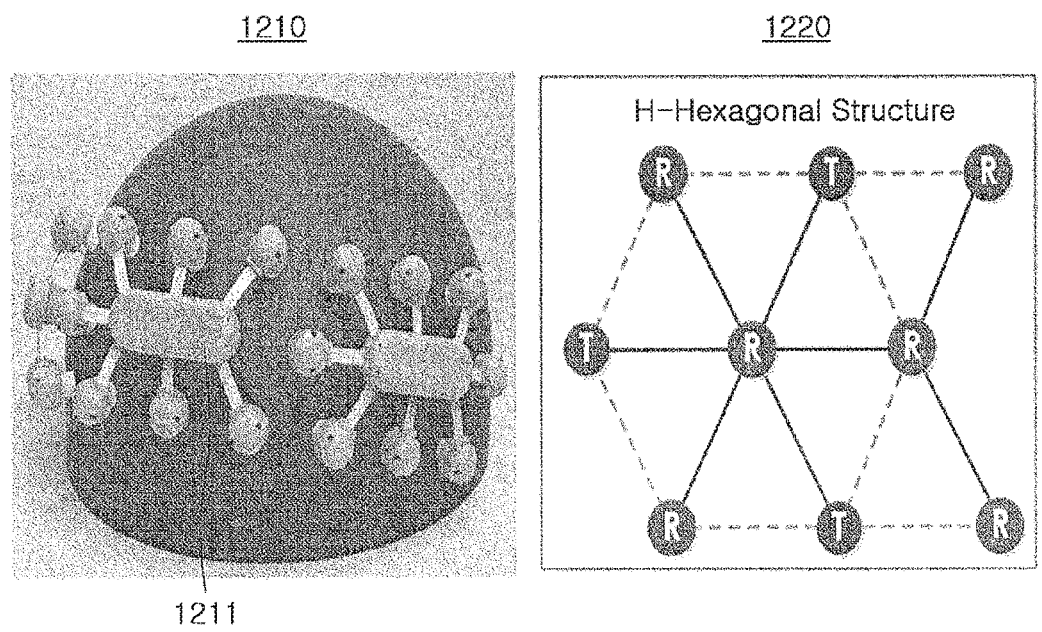
FIG. 12 shows an example of a headset system according to one embodiment of the invention.

FIG. 12 shows an example of a headset system according to one embodiment of the invention.

A photograph 1210 shows a headset system 1211 including holders that are spread at specified equal intervals. The light transmission module 500 or the light reception module 600 may be attached to or detached from the holders of the headset system 1211. The headset system 1211 may be attached to a subject's head through coupling components such as a buckle and a band, and may obtain a biosignal of a living organism in a region where the headset system 1211 is attached.

As shown in a picture 1220, the headset system 1211 may have a H-hexagonal structure (HHS) composed of a plurality of light transmission modules 500 and a plurality of light reception modules 600 as a basic structure. The HHS may be freely expanded to cover the entire head based on the basic structure, as described with reference to the second configuration 720 of FIG. 7. In the picture 1220, T and R may denote the light transmission module 600 and the light reception module 700, respectively.

Figure 13:
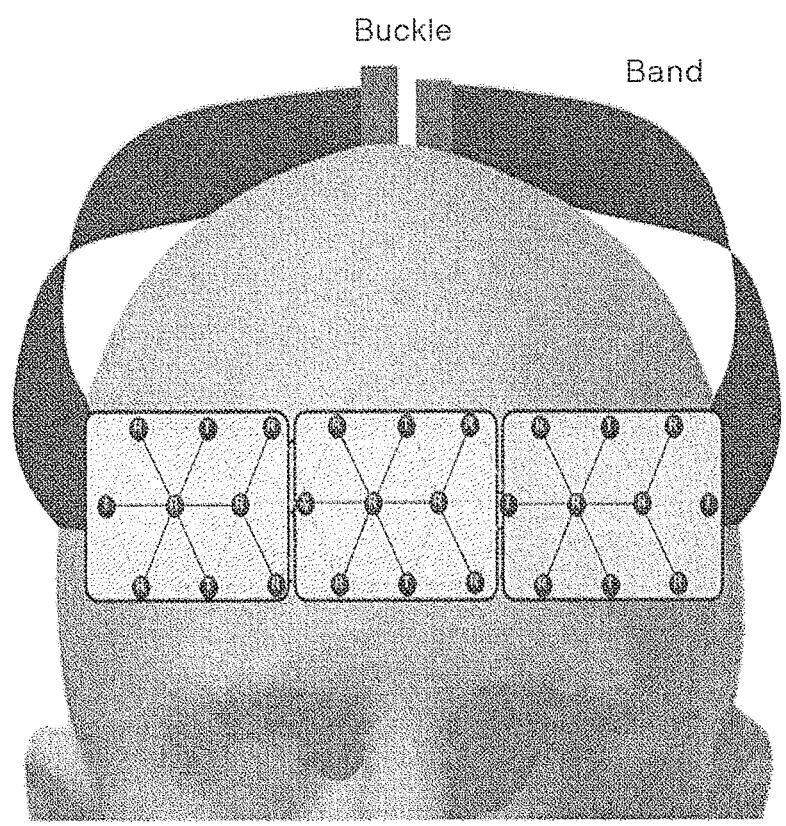
FIG. 13 shows an example of an expanded form of a headset system composed of three basic structures according to one embodiment of the invention.
Figure 14:
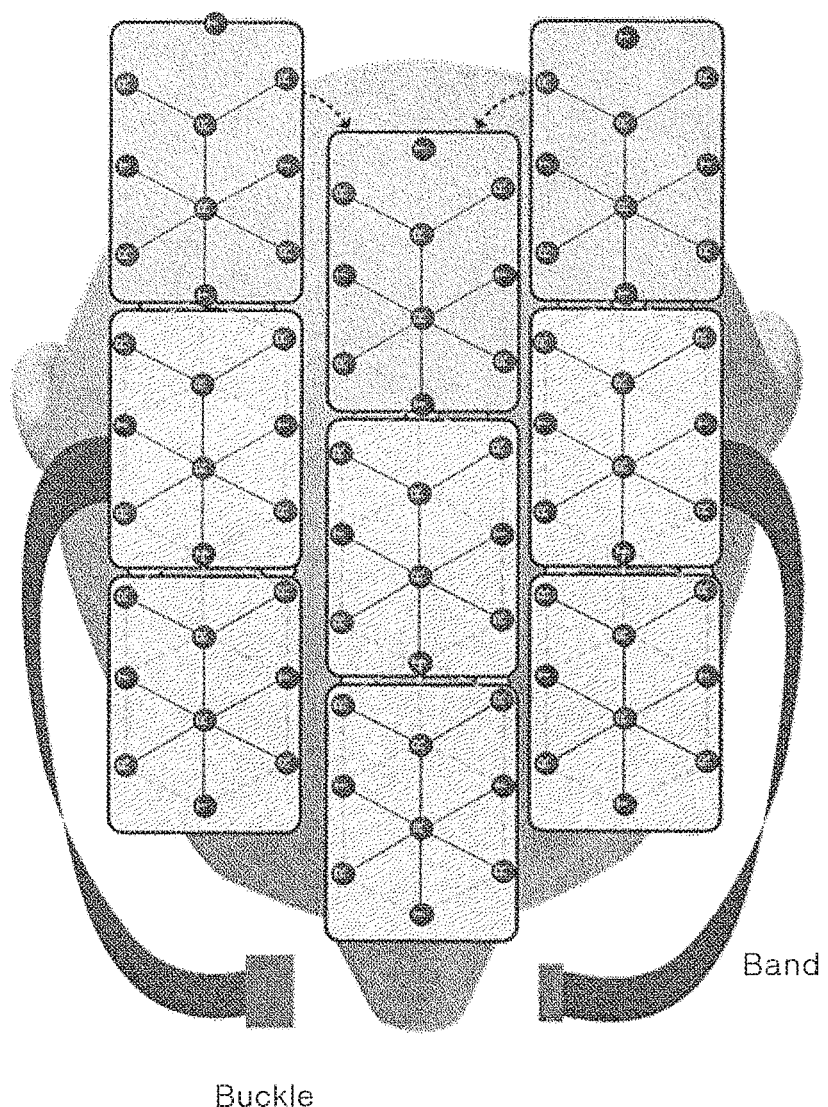
FIG. 14 shows an expanded example of a headset system composed of nine basic structures according to one embodiment of the invention.

FIG. 13 shows an example of an expanded form of a headset system composed of three basic structures according to one embodiment of the invention, and FIG. 14 shows an expanded example of a headset system composed of nine basic structures according to one embodiment of the invention. FIG. 13 shows a headset system configured to measure a biosignal of a frontal lobe region in a human head, and FIG. 14 shows a headset system configured to measure a biosignal from the entire human head. Here, the headset system may be attached to the measured region of the living organism through a buckle and a band.

Pipeline-Structured Matched Filter and Dual Slope Analog-Digital Converter

Figure 15:
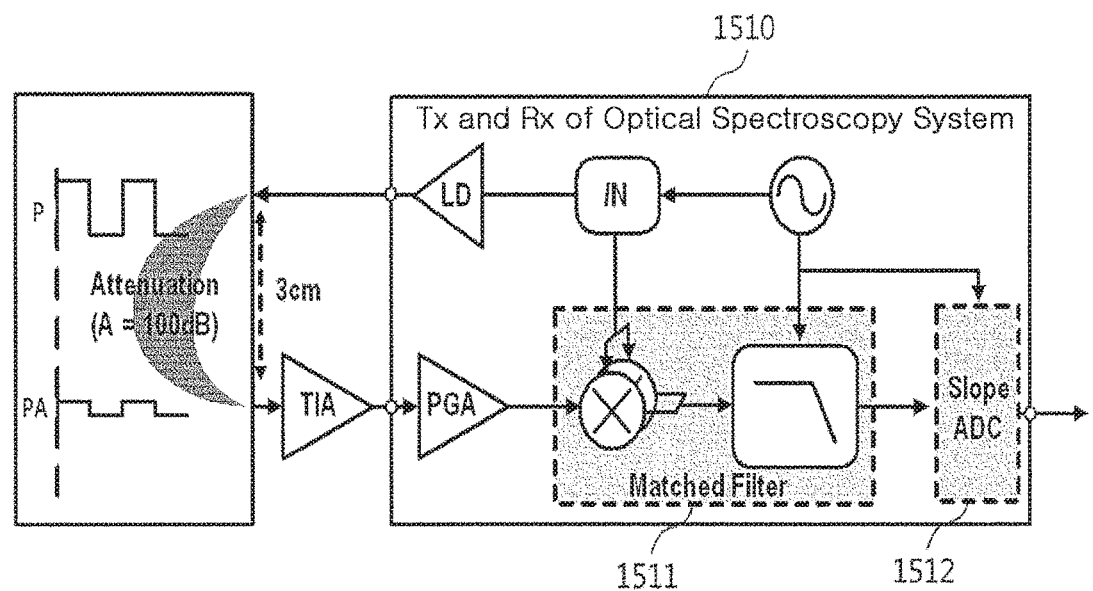
FIG. 15 is a block diagram of Tx and Rx to which a matched filter for an optical spectroscopy system is applied according to one embodiment of the invention.

FIG. 15 is a block diagram of Tx and Rx to which a matched filter for an optical spectroscopy system is applied according to one embodiment of the invention. FIG. 15 shows how a matched filter 1511 is applied to Tx and Rx 1510 of the optical spectroscopy system (particularly, the attachment unit 410 described with reference to FIG. 4). A laser is driven based on the same clock (CLK) to inject light to a brain, and the light attenuated as transmitted through the brain may be amplified using a trans-impedance amplifier (TIA) and a programmable gain amplifier (PGA), and then digitized through the matched filter 1511 and a slope analog-digital converter (ADC) 1512. In this process, the time delay between the transmitted and received signals is negligible because it is very short compared to the duration of Walsh codes. Since the form of noise caused by the scattering occurring in the transmission is the same as that of white Gaussian noise, the influence of the noise can be minimized through the matched filter 1511.

Figure 16:
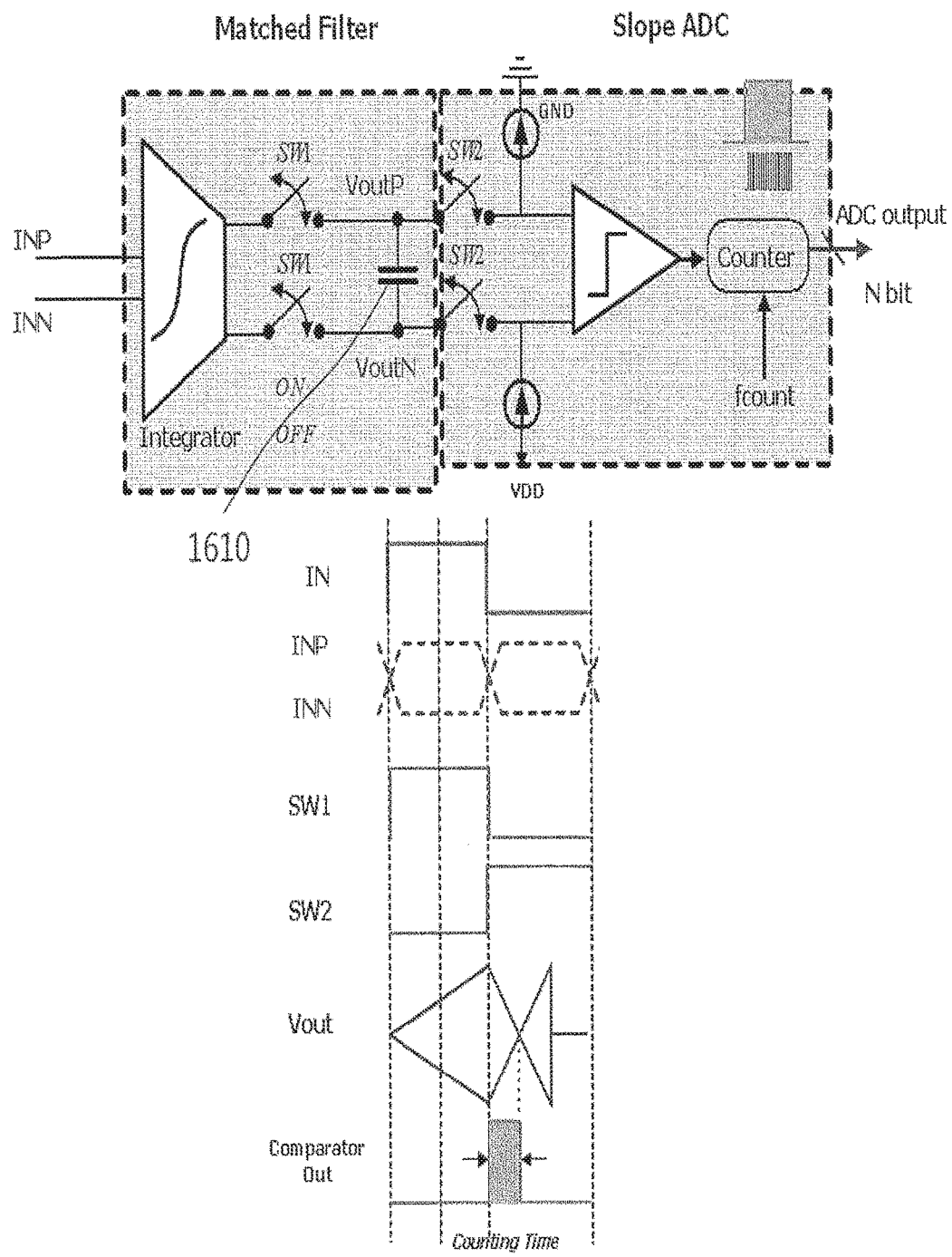
FIG. 16 is a block diagram schematically showing an example in which a matched filter and a slope analog-digital converter are combined according to one embodiment of the invention.

FIG. 16 is a block diagram schematically showing an example in which a matched filter and a slope analog-digital converter are combined according to one embodiment of the invention.

When a matched filter is used, a capacitor 1610 having a considerably large value should be connected to accumulate electric charge in the capacitor 1610 as shown in FIG. 16. An output of the capacitor 1610 is gradually increased as current proportional to input voltage flows from an output of a transconductor (Gm) amplifier to the capacitor 1610 while SW1 is 1. The electric charge stored in the capacitor 1610 is gradually decreased through the current source from the time when SW1 becomes 0 and SW2 becomes 1, and the time when the differential signals cross each other is detected using the duration in which the comparator is maintained at 1 based on the CLK. In the duration, the counter operates based on the clock and converts the time into digital codes, which may be referred to as a slope ADC structure. Since the slope ADC structure implemented after the matched filter can realize the ADC without the need for additional capacitors, it is effective in terms of size and has a high degree of integration in implementing a multi-channel receiver.

Figure 17:
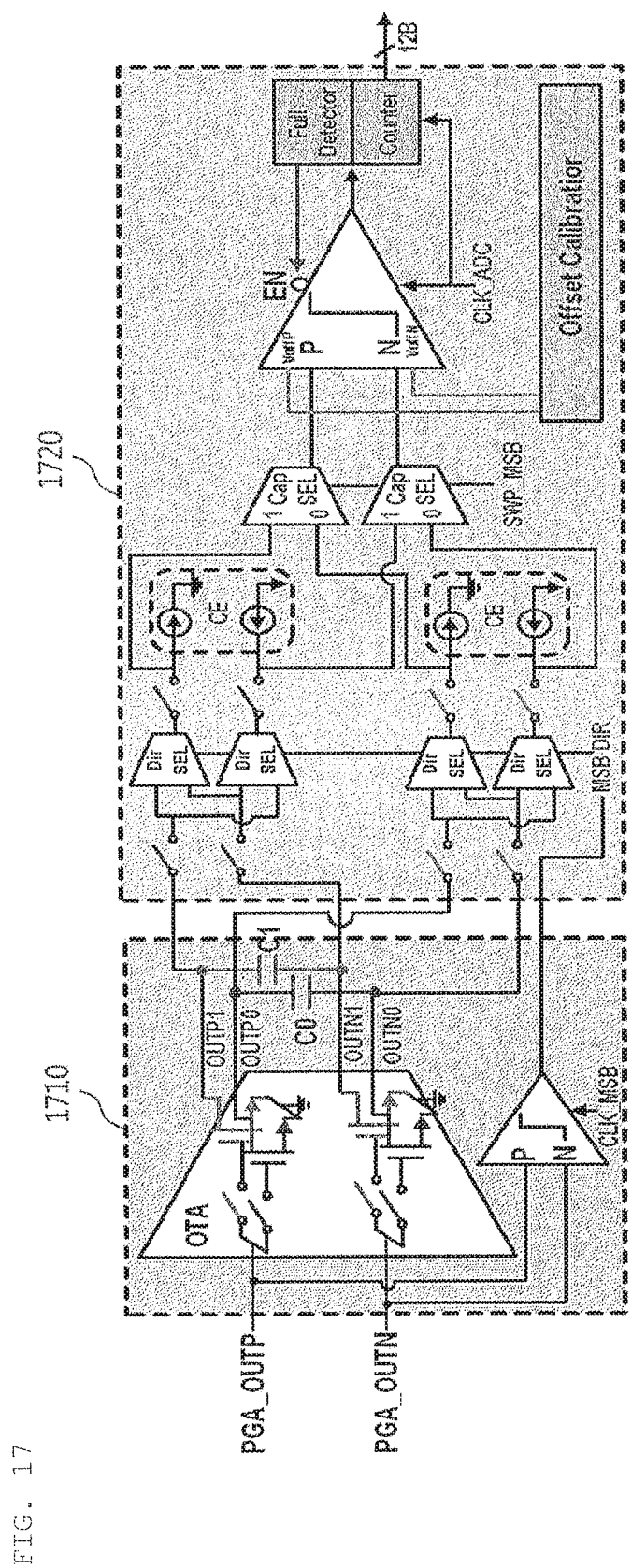
FIG. 17 shows an example of a matched filter applied in a pipeline structure according to one embodiment of the invention.
Figure 18:
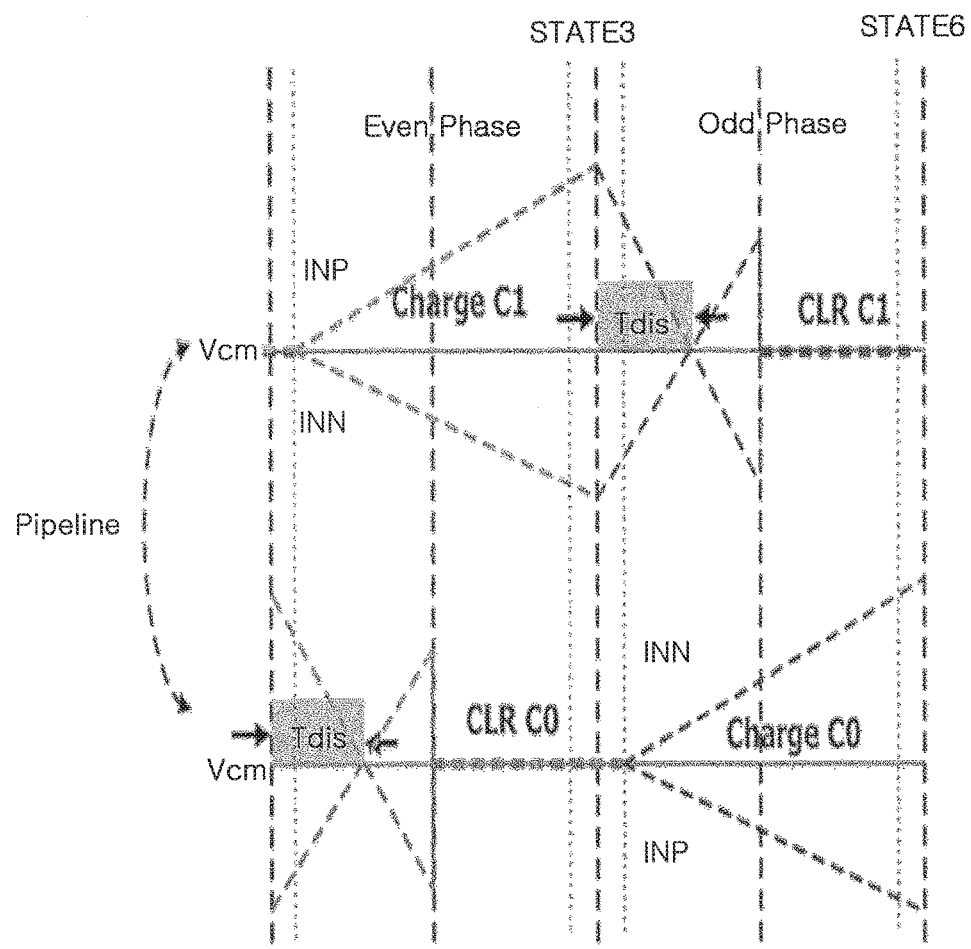
FIG. 18 shows a time diagram in the matched filter applied in the pipeline structure according to one embodiment of the invention.

FIG. 17 shows an example of a matched filter applied in a pipeline structure according to one embodiment of the invention, and FIG. 18 shows a time diagram in the matched filter applied in the pipeline structure according to one embodiment of the invention.

When one capacitor is used, input data is stored in the capacitor in even phases and the stored charge is extracted in odd phases. Thus, since the capacitor cannot store the input data in odd phases, there arises a problem that the matched filter structure should be implemented using only half of a bit period of inputted Walsh codes.

Accordingly, a switch-based pipeline structure is realized at a voltage node by modifying the last stage within the transconductor (Gm) into a pipeline structure, as shown in FIG. 17. As shown in FIG. 18, when a capacitor 1 (C1) is in the phase in which electric charge is stored, discharging occurs in a capacitor 2 (C2), which may mean that the capacitors can smoothly operate in the form of a dual slope ADC. Since they are switched at the voltage node, there are no more instantaneously generated current leakage lines (which are caused by non-ideal rising and falling edges of the switching time), and thus they can operate without current leakage. This allows a matched filter structure to be implemented for the same time as the bit period of the inputted Walsh codes, and minimizes current leakage and nonlinear effects occurring in the switching circuit by implementing the pipeline structure at the voltage node.

FIG. 16 is a diagram showing a simplified model in which only one phase plane of the pipeline structure is shown, and FIG. 17 shows the pipeline structure based on the diagram. Even phases may correspond to the case where SW1 is 1, and odd phases may correspond to the case where SW2 is 1. In both cases, it can be seen that an IN signal and SW1 and SW2 signals are equally aligned as the inputs. This is because the edges are aligned since the signals are generated based on the same clock, and the matched filter structure can be implemented based on these characteristics.

Figure 19:
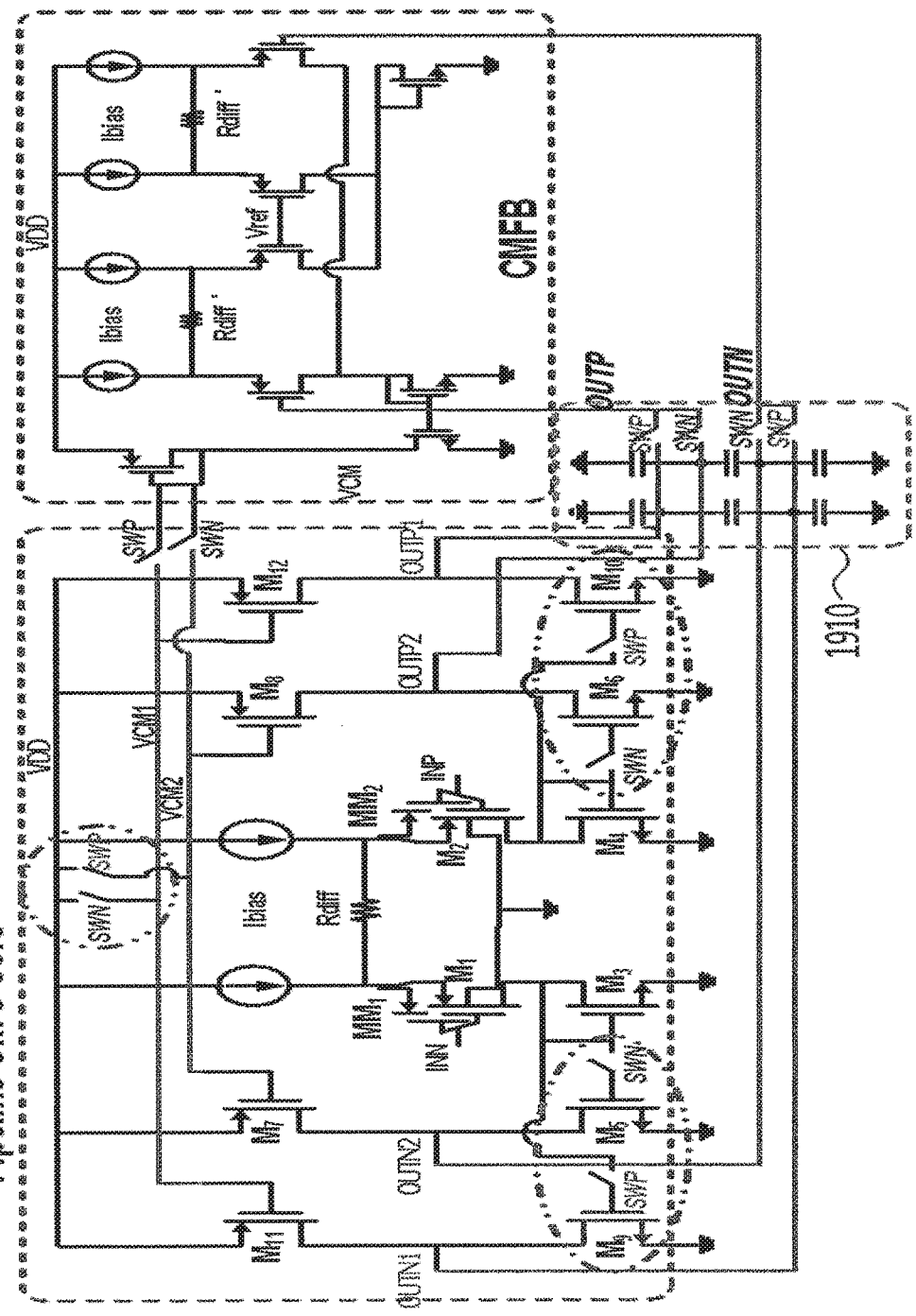
FIG. 19 shows a detailed schematic structure of a pipeline transconductor (Gm) amplifier according to one embodiment of the invention.

FIG. 19 shows a detailed schematic structure of a pipeline transconductor (Gm) amplifier according to one embodiment of the invention. While SW is turned on, current dependent on input voltage is accumulated in a capacitor. For linear accumulation, the bandwidth of an output node of Gm-C should exist in a very low frequency band. To this end, the size of the capacitor should be large and the Gm value of the amplifier should be small. Since the size of the capacitor cannot be infinitely increased, it is necessary to implement the small value of Gm. The value of Gm can be reduced by dividing the amount of current generated in the circuit according to the inputs by means of a pair of input MOSs, and keeping a mirror ratio small until the final output stage. OUT1 and OUT2, which are outputs of the pipeline structure, may accumulate electric charge in capacitors on the left side in a first dashed line box 1910 when SWP is 1, and in capacitors on the right side in the first dashed line box 1910 when SWN is 1. As above, one common mode feedback circuit may be used such that it is switched for each phase, thereby reducing the size of the matching circuit.

Figure 20:
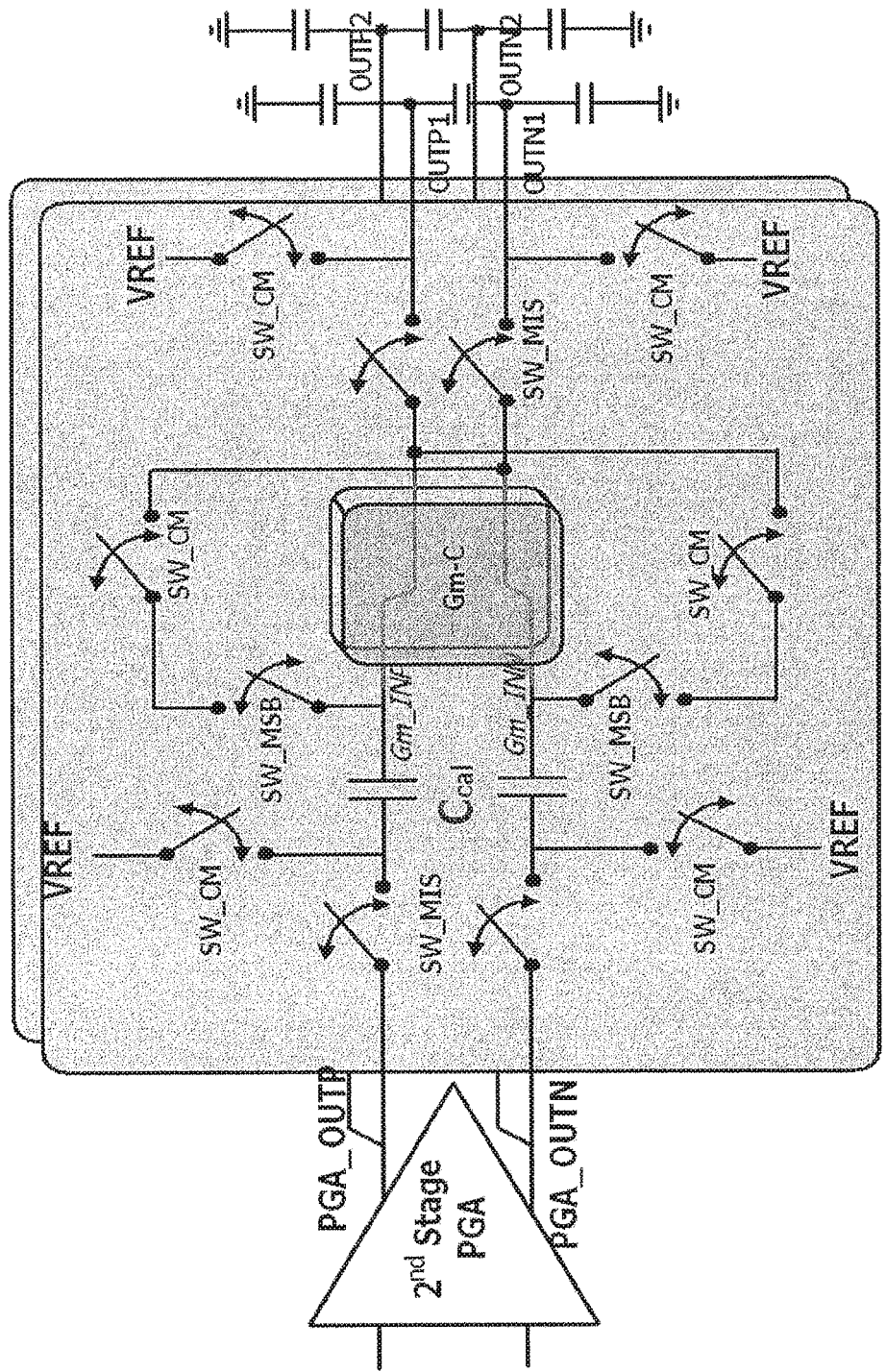
FIG. 20 shows a structure for calibrating a DC offset caused by a Gm-C mismatch according to one embodiment of the invention.

FIG. 20 shows a structure for calibrating a DC offset caused by a Gm-C mismatch according to one embodiment of the invention.

A Gm-C amplifier itself is a MOS-based amplifier and needs to be prepared for a size mismatch between differential MOSs, which occurs while proceeding with the process. To this end, in the periods excluding the time when electric charge is accumulated in and drained from capacitors, a switch for mismatch calibration is used to sample the offset when SW_MIS is 0 and SW_CM is 1, and then connected in the opposite phase when SW_MIS is 1 and SW_CM is 0, thereby enabling compensation for the mismatch.

Figure 21:
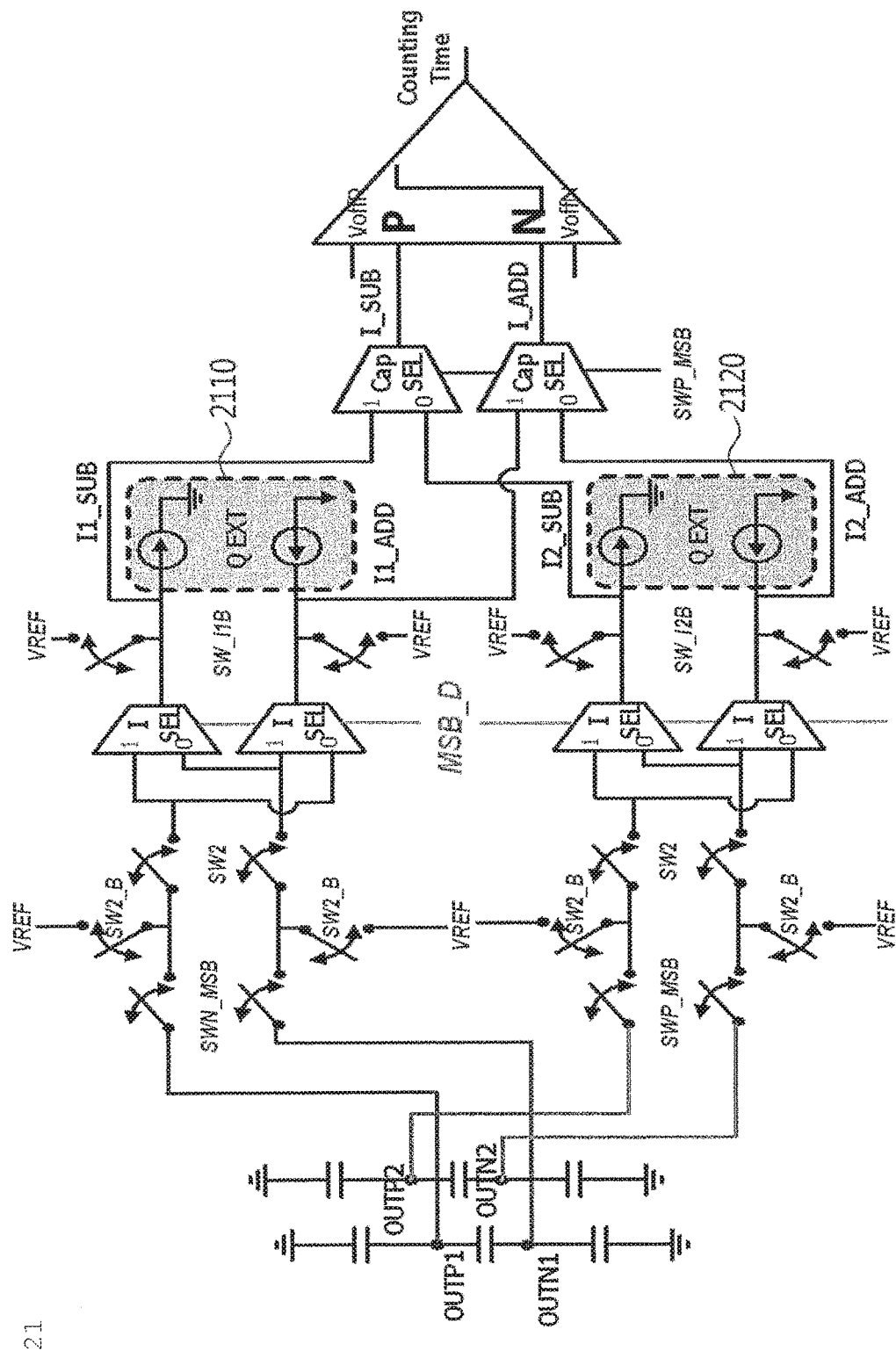
FIG. 21 shows a dual current source structure for discharge in a pipeline Gm-C structure according to one embodiment of the invention.

FIG. 21 shows a dual current source structure for discharge in a pipeline Gm-C structure according to one embodiment of the invention.

A slope ADC performs its operation as electric charge accumulated in capacitors is discharged at different times in the form of a pipeline. If one current source is used to drain the charge, the different capacitors are connected to the current source through a SW-based multiplexer, or to a common voltage source Vref. In this case, since the multiplexer is a MOS-based SW and its resistance is not infinitely large in an OFF state, a current leakage phenomenon occurs so that the charge leaks in the charge accumulation phase. Accordingly, as shown in FIG. 21, two different current sources 2110 and 2020 may be connected to the respective capacitors for the pipeline to prevent the current node from being shared.

Figure 22:
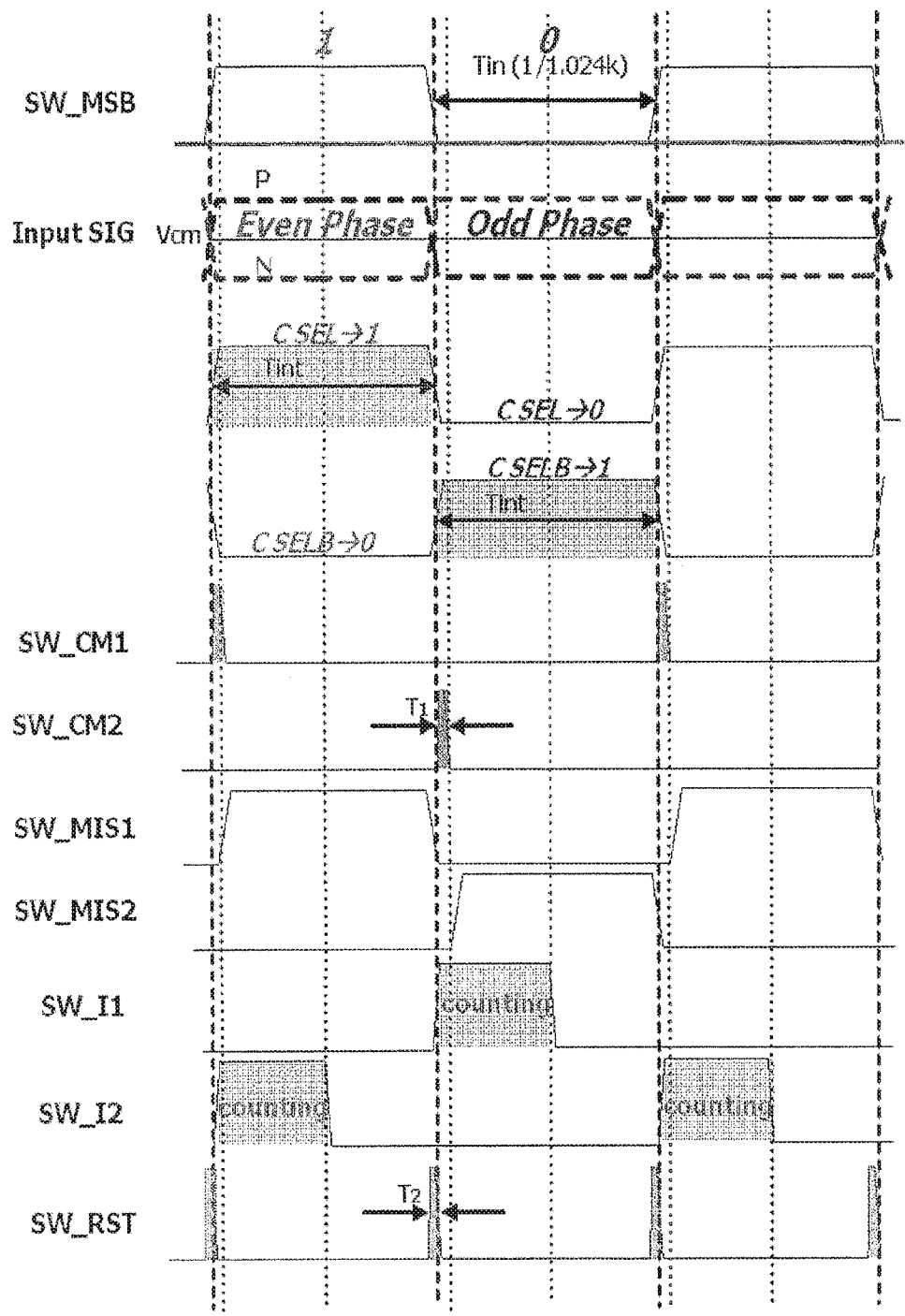
FIG. 22 shows a switching time diagram for a pipeline Gm-C based matched filter structure according to one embodiment of the invention.

FIG. 22 shows a switching time diagram for a pipeline Gm-C based matched filter structure according to one embodiment of the invention. FIG. 22 shows an example in which switching signals required to configure the pipeline structure are implemented by a clock generator that is digitally synthesized based on a single clock (CLK).

A method for controlling the optical spectroscopy system according to one embodiment of the invention may comprise the following steps (1) and (2).

In the step (1), a pipeline-structured matched filter included in the optical spectroscopy system may sequentially connect input voltage, which is transmitted through an amplifier, to a first capacitor and a second capacitor through a first switch stage.

In the step (2), a dual slope analog-digital converter included in the optical spectroscopy system may sequentially receive electric charge stored in the first and second capacitors through a second switch stage and digitize the input voltage.

Here, the first and second switch stages may sequentially switch the connection to the first and second capacitors based on a clock generated according to a Walsh code bit period, and may be connected to the different capacitors among the first and second capacitors at the same clock, respectively.

According to another embodiment of the invention, the method for controlling the optical spectroscopy system may further comprise the steps of (3) emitting light to a specific region of a subject based on the clock generated according to the Walsh code bit period, and (4) collecting light coming through the specific region, in addition to the steps (1) and (2). Here, the steps (3) and (4) may be performed before the above-described steps (1) and (2), and may be performed by a light transmission unit (e.g., the light transmission unit 411) and a light reception unit (e.g., the light reception unit 412), respectively. Here, the matched filter and the dual slope analog-digital converter may be included in the light reception unit and operated based on the clock used in the light transmission unit.

The light reception unit may comprise a TIA (Trans-Impedance Amplifier) and a PGA (Programmable Gain Amplifier) as the above-described amplifier.

According to yet another embodiment of the invention, the method for controlling the optical spectroscopy system may comprise the step of (5) switching input voltage transmitted through the amplifier in each phase and sequentially connecting the input voltage to a first capacitor and a second capacitor, and sequentially receiving electric charge stored in the first and second capacitors according to the phase and digitizing the input voltage, instead of the above-described steps (1) and (2). For example, the step (5) may be performed by the common mode feedback circuit described with reference to FIG. 19.

According to still another embodiment of the invention, the method for controlling the optical spectroscopy system may further comprise the step of (6) compensating for a size mismatch between differential MOSs in periods excluding the time when the first and second capacitors are charged and discharged. The step (6) may be performed by a mismatch adjustment switch stage and a mismatch adjustment capacitor, which may be further included in the optical spectroscopy system. For example, the input voltage includes first voltage and second voltage, which are outputs of the amplifier, and when the first input voltage is 1 and the second input voltage is 0, the mismatch adjustment switch stage may sample a DC offset size existing in the amplifier itself to the mismatch adjustment capacitor, and then connect the sampled voltage to the first and second capacitors in the opposite phase, thereby compensating for the size mismatch between the differential MOSs.

Optical Spectroscopy System Operating as a Walsh Code-Based Single CLK Generator An optical spectroscopy system according to the present embodiments may use a Walsh code-based single CLK generator. As for Walsh codes, which are among the codes used for code division multiplexing, the number of orthogonal codes is determined according to the code length, and the correlation between the codes is zero.

Thus, when the Walsh codes are used to modulate a sequence of lasers of light transmission modules in the optical spectroscopy system, one light reception module can demodulate and extract hemodynamics information of various regions without interference between channels.

Figure 23:
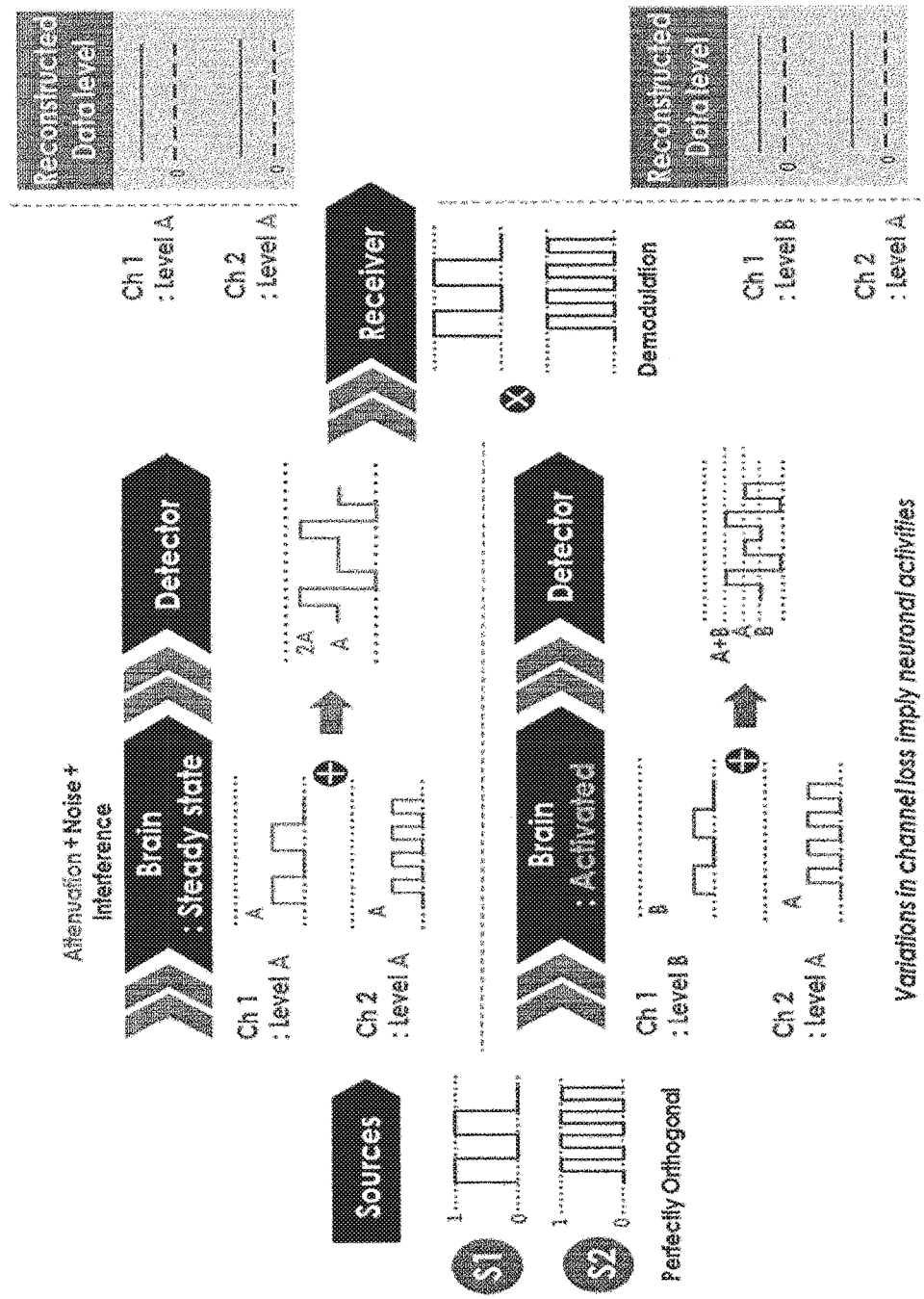
FIG. 23 shows an example of an application aspect of CDMA modulation according to one embodiment of the invention.

FIG. 23 shows an example of an application aspect of CDMA modulation according to one embodiment of the invention.

In FIG. 23, when light emitted from a source 1 (S1) and a source 2 (S2) passes through a living organism and enters a detector, it is not possible to distinguish the light emitted from S1 and that emitted from S2 according to a principle of near-infrared spectroscopy (NIRS). Thus, in the optical spectroscopy system according to the embodiments of the invention, light can be emitted from each light source as code-modulated with perfectly orthogonal codes (e.g., the above-described Walsh codes).

Further, the light emitted from the detector can be demodulated with the same codes as those of the light source, so that it is possible to distinguish which light source has emitted the light. In this manner, the optical spectroscopy system can use light entering a detector from a plurality of light sources to accurately determine which part of the brain is activated to change the concentrations of oxyhemoglobin and incident light.

TABLE 1 shows the factors that cause changes in an oxygen saturation level in human blood and information on the corresponding frequency bands.

TABLE 1

| No. | Artifact | Source | Freq. (Hz) |
|---|---|---|---|
| 1 | Laser temperature drift | Temperature dependency of laser | |
| 2 | Very low frequency oscillation | — | 0.04 |
| 3 | Low freq. spontaneous physiological oscillations (LFO, vasomotor wave, or Mayer's wave) | Relate to arterial blood pressure | 0.1 |

TABLE 1-continued

| No. | Artifact | Source | Freq. (Hz) |
|---|---|---|---|
| 4 | Respiration frequency | Respiration (Adult: 12-20 cycle/min) | 0.2 |
| 5 | Cardiac oscillation | Heart beat (Adult: 60-80) | 1 |

The changes in the blood oxygen saturation level occurring in a human body are caused by the factors shown in TABLE 1, and it can be seen that the changes are considerably slow since they are not more frequent than 1 Hz.

Figure 24:
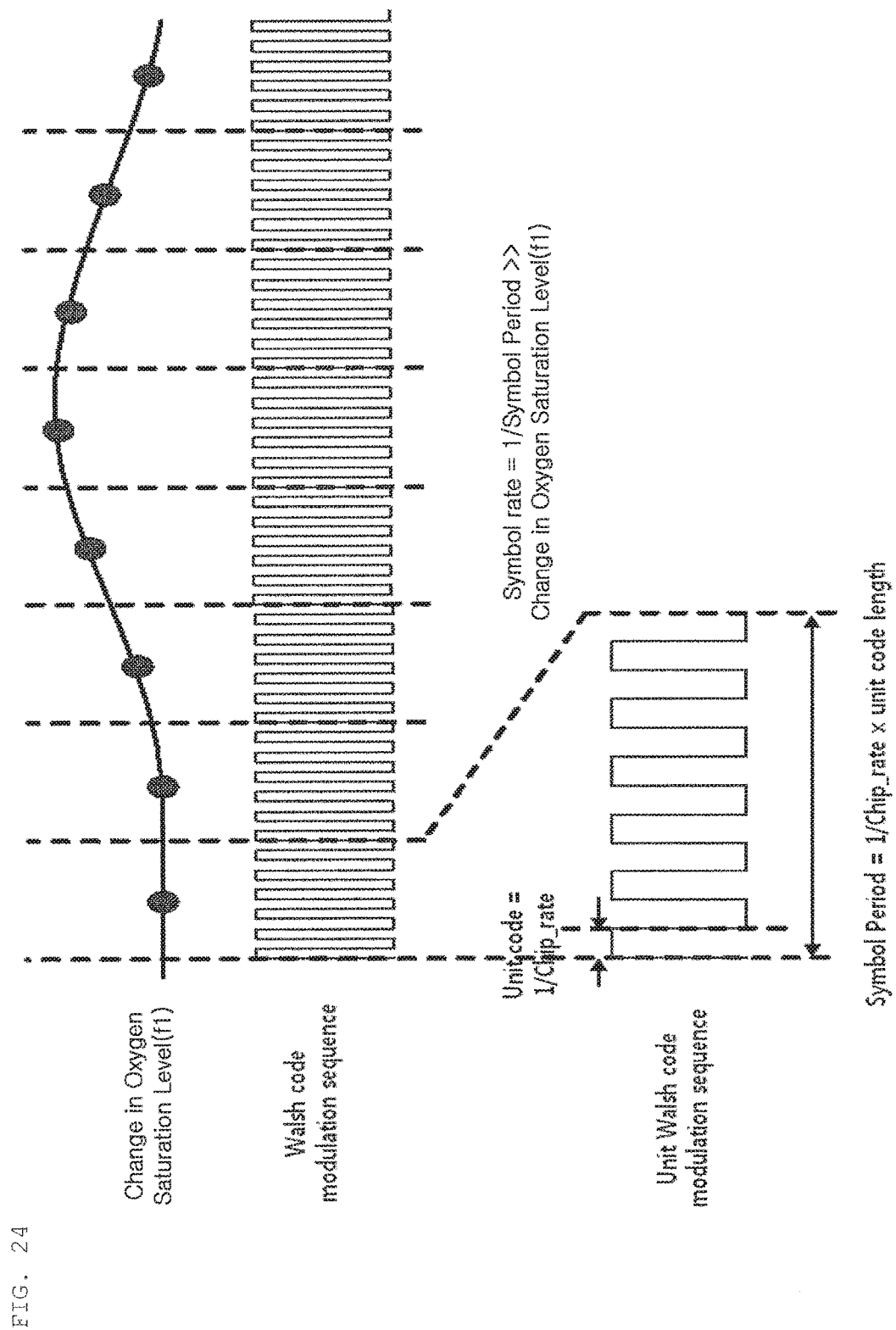
FIG. 24 shows an example of an aspect of modulating changes in a blood oxygen saturation level with codes according to one embodiment of the invention.

FIG. 24 shows an example of an aspect of modulating changes in a blood oxygen saturation level with codes according to one embodiment of the invention. First, the following parameter values should be determined in order to measure signals using a code-based modulation technique in the optical spectroscopy system.

The chip rate and length of the codes used for the modulation may be determined in consideration of the symbol rate at the time of demodulation and the hemodynamic frequency in the human body. Assuming that a unit Walsh code modulation sequence is repeated and that there is little change in the oxygen saturation level, the result of demodulation in the received signals can be obtained because it is possible to correctly recover the signals in the body. Further, the chip rate and unit code length may be adjusted according to the number of channels to be independently received and the specifications of the system.

Figure 25:
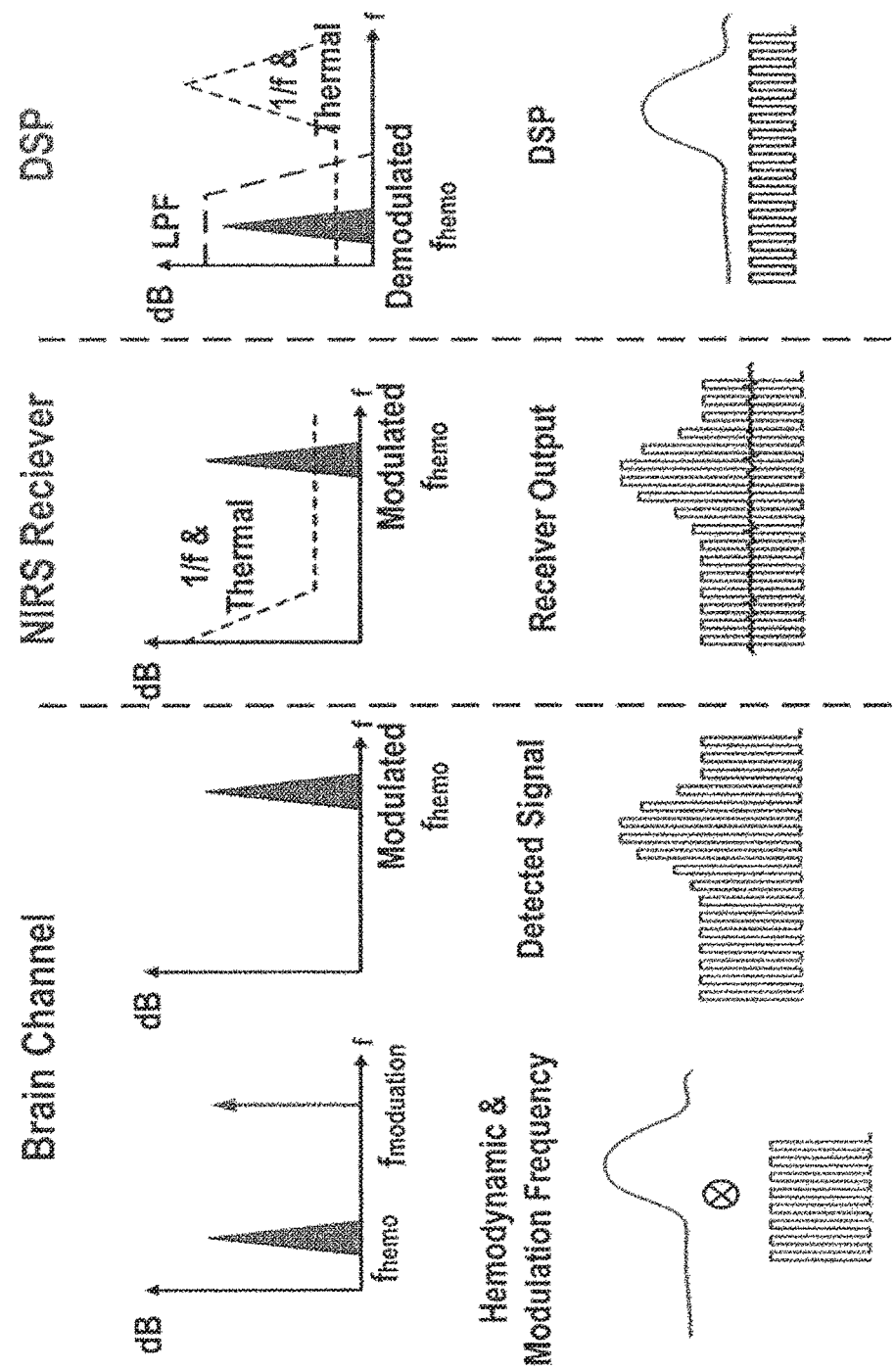
FIG. 25 shows an example of a flowchart for extracting a hemodynamic signal except for low noise when proceeding with code-based modulation and demodulation according to one embodiment of the invention.

FIG. 25 shows an example of a flowchart for extracting a hemodynamic signal except for low noise when proceeding with code-based modulation and demodulation according to one embodiment of the invention.

The form of laser light modulated with Walsh codes is changed according to a hemodynamic change in a path through which the light travels from when it enters a living body until it is detected by a detector. It can be said that the form corresponds to the Walsh codes being mixed with the hemodynamic signals. Although hemodynamic information corresponds to signals of less than about 1 Hz, the Walsh codes of a higher frequency band are used and thus the tones of the signals move to a high frequency band. Accordingly, when an operation related to analog amplification is performed in a chip, there is immunity to 1/f noise components, which are large noises of a low frequency band generated in the circuit itself. After a demodulation process, the noise-minimized hemodynamic signals may be extracted through low pass filtering (similarly to a chopping structure).

Matched Filter-Based Data Sampling

White noises existing in input signals and circuits may be accumulated in a continuous time domain based on an oversampling effect, so that one piece of data may be extracted for each bit period. This technology is employed for optical communication systems, and uses a matched filter structure that can extract a signal with a maximum signal-to-noise ratio (SNR). In order to implement the matched filter structure, there is a precondition that bits received as inputs should be exactly synchronized with a sampling clock. Thus, in the optical communication systems, the clock is controlled by further using a phase locked loop (PLL) at a reception stage.

However, in the embodiments of the invention, a signal separated by using a reference clock in an integrated circuit itself is injected into a subject's head, and the injected signal is transmitted through the subject's head to a receiver (e.g., the light reception module 600). (That is, light emission and detection are both performed in one system.) Therefore, accumulation periods may be generated in the same synchronization using the same separated signal in the integrated circuit, so that the matched filter may be implemented with a simpler structure.

As an oversampling rate N is increased, the noise of a measured signal is reduced to 1/square root N. Since the result of infinitely increasing N is the same as the accumulated form, the white Gaussian noise generated within the signals and the chip (integrated circuit) may be maximally reduced.

Figure 26:
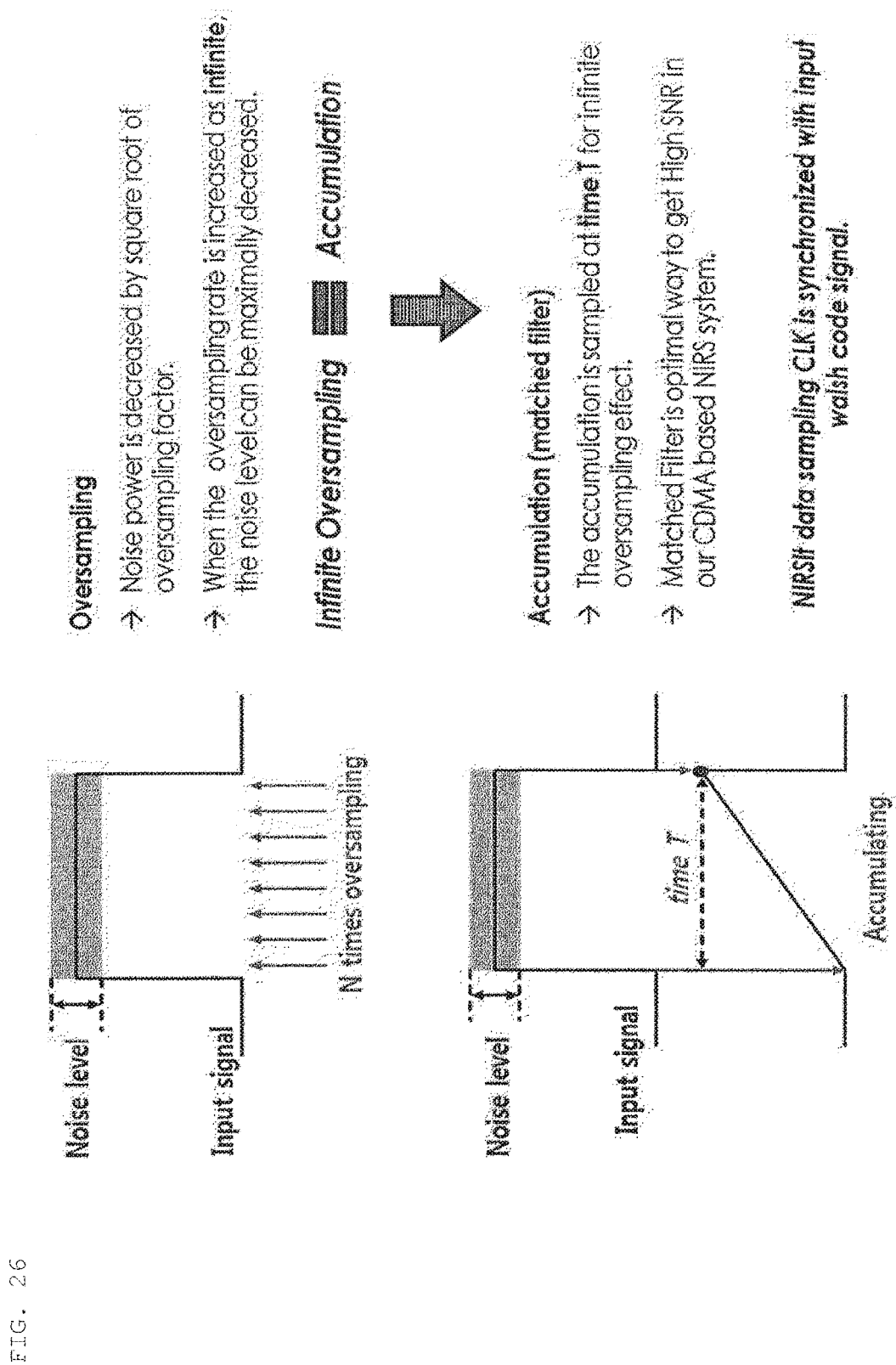
FIG. 26 shows an oversampling effect and a matched filter effect according to one embodiment of the invention.
Figure 27:
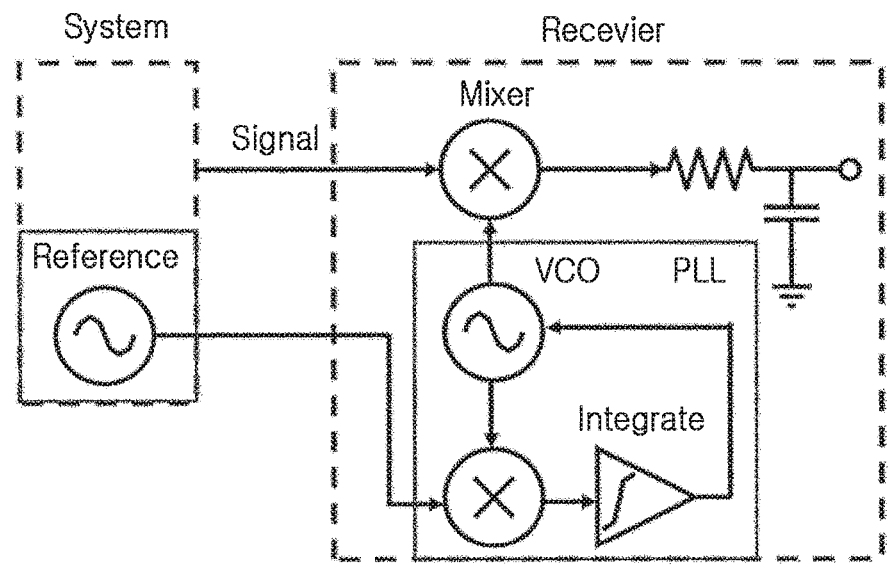
FIG. 27 shows a comparison between a matched filter structure of prior art and that according to one embodiment of the invention.
Figure 27:
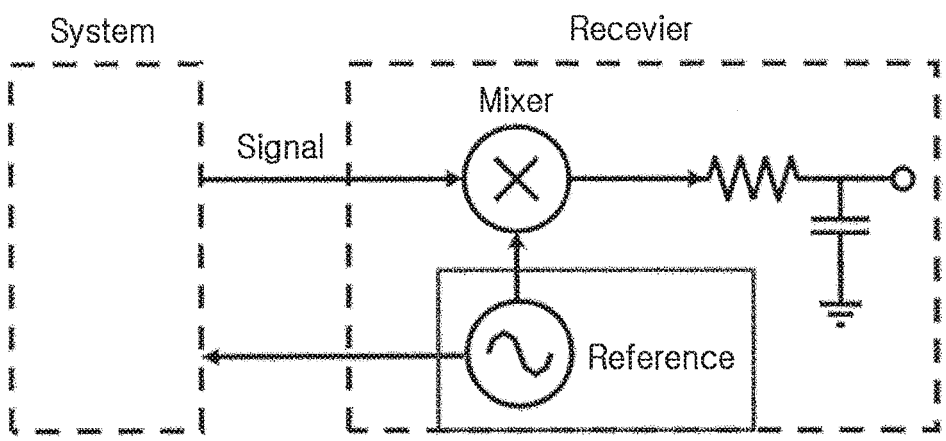

FIG. 26 shows an oversampling effect and a matched filter effect according to one embodiment of the invention, and FIG. 27 shows a comparison between a matched filter structure of prior art and that according to one embodiment of the invention.

In order to implement a matched filter structure, there is a precondition that signals received as inputs should be exactly synchronized with a clock used in sampling. In a general communication system (a system 2710 of prior art), a reference clock is external to a receiver, and the receiver should further use additional circuitry such as a PLL to adjust sampling synchronization in order to synchronize with the data received at an input of the receiver. However, in an integrated circuit of an optical spectroscopy system 2720 according to the present embodiment, a modulation sequence is generated using a reference clock of the integrated circuit itself, and the generated signal only has its own attenuation while it is injected into a brain channel of a subject (corresponding to an external system of prior art) and then transmitted through a cerebral cortex to a receiver. Accordingly, it can be assumed that the received input signals are synchronized with the sampled clock, and thus the function of the matched filter can be implemented with a relatively simple structure in the optical spectroscopy system 2720 according to the present embodiment.

A method for controlling the optical spectroscopy system according to one embodiment of the invention may comprise the steps of emitting light to a specific region of a subject using a plurality of light sources in a light transmission unit (e.g., the light transmission unit 411) included in the optical spectroscopy system, wherein the light emitted from the plurality of light sources is code-modulated using Walsh codes, and detecting light coming through the specific region in a light reception unit (e.g., the light reception unit 412) included in the optical spectroscopy system, wherein the light is demodulated using the Walsh codes to distinguish the light sources. Here, the control method may further comprise the step of extracting one piece of data for each bit period by accumulating input signals in a continuous time domain using a reference clock used for the light emission in a matched filter included in the light reception unit as a sampling clock.

A method for controlling the optical spectroscopy system according to another embodiment of the invention may comprise the steps of emitting light to a specific region of a subject in a light transmission unit of the optical spectroscopy system, and detecting light coming through the specific region in a light reception unit of the optical spectroscopy system. Here, in the step of detecting light, a matched filter included in the light reception unit may extract one piece of data for each bit period by accumulating input signals in a continuous time domain using a reference clock used for the light emission as a sampling clock.

The matched filter of each embodiment may match bits received as inputs with light emitted using the reference clock, so that synchronization between the bits received as inputs and the reference clock may be achieved without using any additional PLL.

Optical Spectroscopy System Using Time-Divided Spread Spectrum Codes (TDSSC)

Depending on the type of person, the degree of light absorption varies with the curvature of the head, the thickness of layers constituting the head, the color of skin, and the like. Thus, if the same laser power is applied to the entire region of the head and to all persons, a situation may occur in which light transmitted through a cerebrum in a specific measured region is all absorbed before reaching the surface of the head, so that the measurement may not be possible. In this regard, it is possible to allow the light transmitted through the cerebrum to reach the surface of the head by making the laser power strong. However, the laser power cannot be infinitely increased because there is a limitation on the power of laser that can be maximally injected into the human body.

Figure 28:
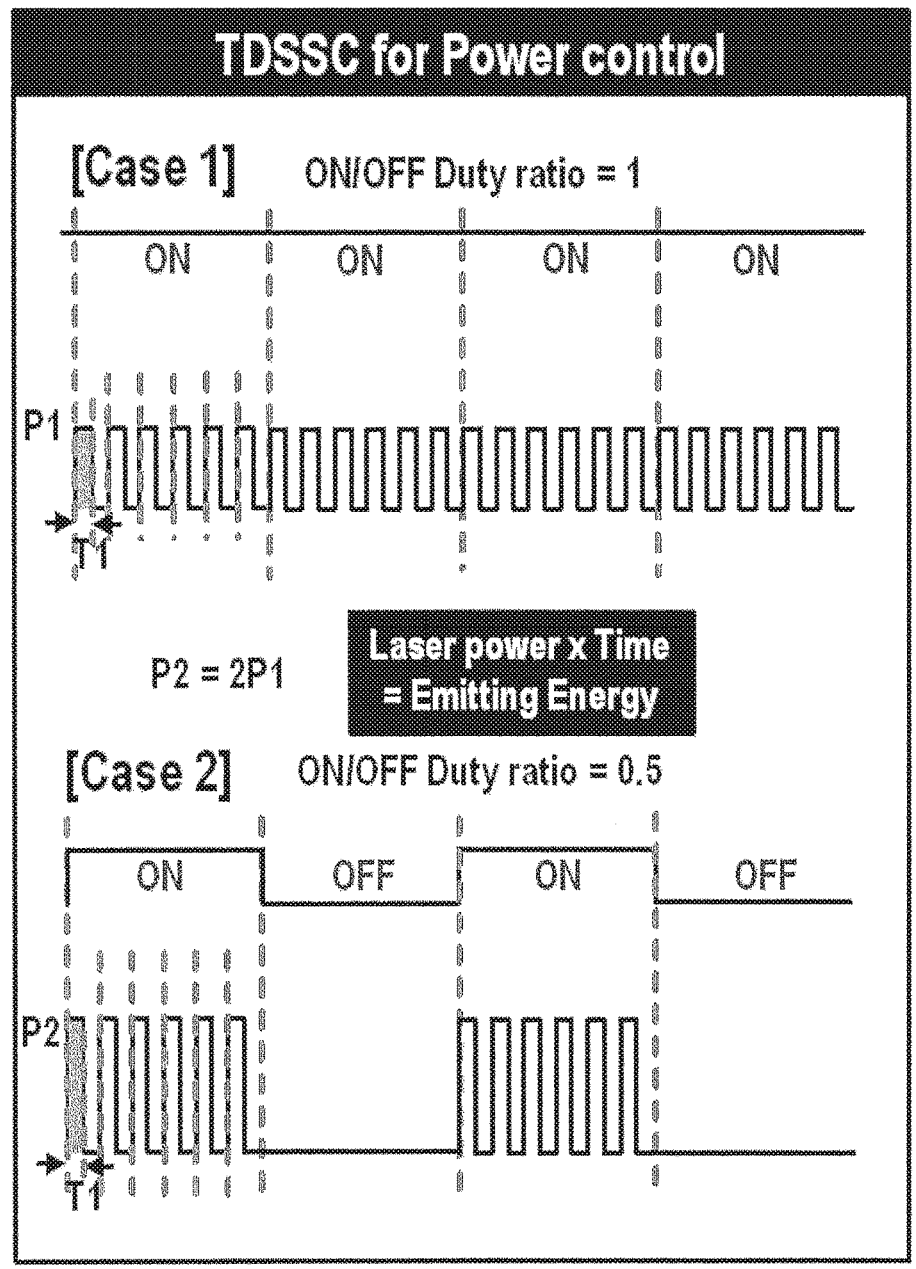
FIG. 28 shows an application example of time-divided spread spectrum codes according to one embodiment of the invention.

FIG. 28 shows an application example of time-divided spread spectrum codes according to one embodiment of the invention. As described above, since light injected into a human body may be represented as the number of photons per unit time, intense light may be injected into the human body if the duration in which the light is injected is adjusted so that a small amount of photons are instantaneously injected. Thus, the photons can reach the surface of the head by increasing the instantaneous intensity of the light while maintaining the entire amount of energy. Further, it is possible to design the system so that more intense light is injected into the human body while reducing the duration of 1 of Walsh codes per unit time. For example, if an on/off duty ratio is adjusted on the assumption that the same energy is injected, spread codes are simultaneously started and injected and then simultaneously turned off, thereby maintaining the orthogonality between the codes. It is assumed in FIG. 28 that on/off duty ratios are 1 and 0.5 in Cases 1 and 2, respectively. Laser injection time for the duty ratio of 0.5 is twice as small as that for the duty ratio of 1, so that the signal magnitude of the injected Walsh codes can be relatively increased (P2=P1×2). The time-divided spread spectrum codes (TDSSC) may be implemented with a structure capable of adjusting the duty of Walsh codes and laser power within the integrated circuit.

Multi-Channel Laser and LED Driver

In the light transmission module according to the present embodiment, it is possible to adjust power from 5.2 mA to 14.9 mA in 256 stages with a dual wavelength laser and a LED driver. Further, there is an option to double the scale, and it is possible to output signals modulated with Walsh codes according to each wavelength.

Figure 29:
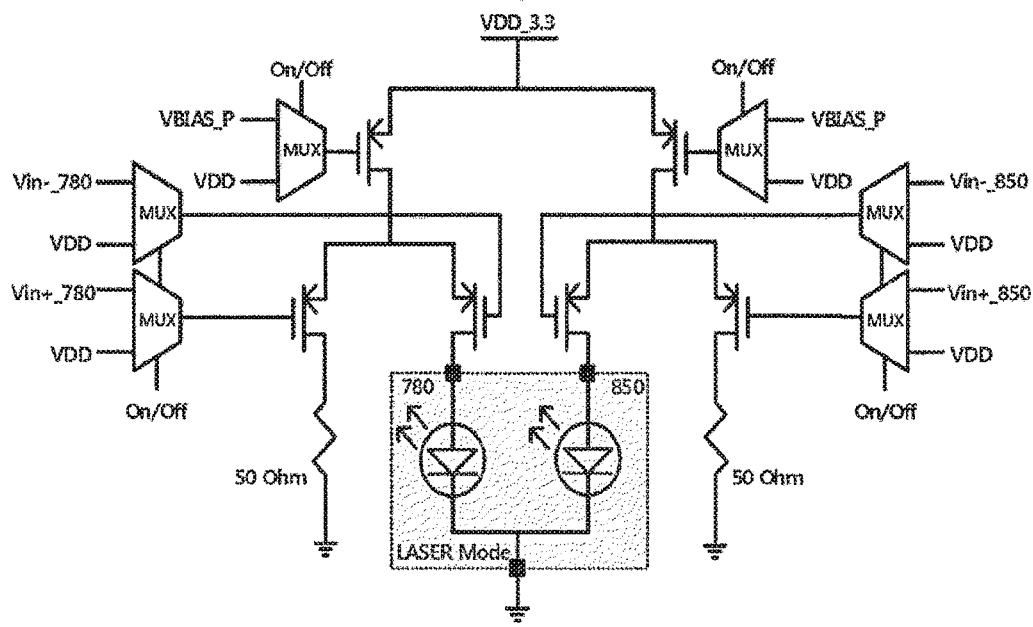
FIG. 29 shows structures of a dual wavelength laser driver and a LED driver according to one embodiment of the invention.
Figure 29:
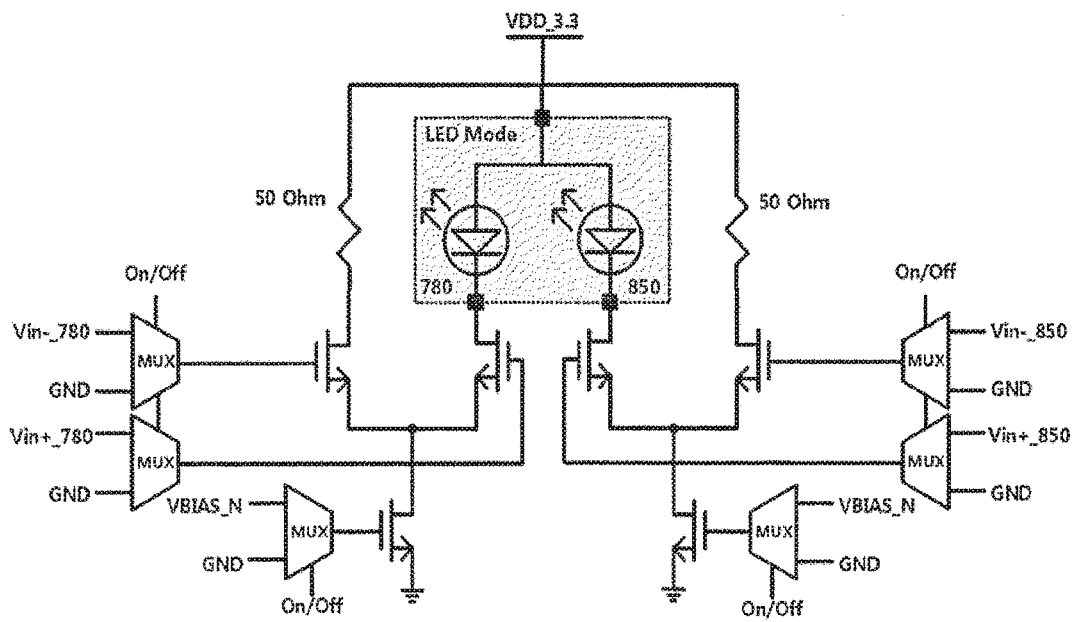

FIG. 29 shows structures of a dual wavelength laser driver and a LED driver according to one embodiment of the invention. FIG. 29 shows a dual wavelength laser driver 2910, which is a dual VCSEL (Vertical Cavity Surface Emitting Laser) device, and a dual wavelength LED driver 2920, which is a dual LED device. Here, the dual wavelength laser driver 2910 and the dual wavelength LED driver 2920 may be connected to a phase of one of positive and negative electrodes. In FIG. 29, the dual wavelength laser driver 2910 is connected to ground together with the positive electrode, and the dual wavelength LED driver 2920 is connected to VDD together with the negative electrode. Thus, in order to modulate the dual wavelength laser driver 2910 (i.e., the dual VCSEL) and the dual wavelength LED driver 2920 with different codes, they should be implemented using different drivers.

Figure 30:
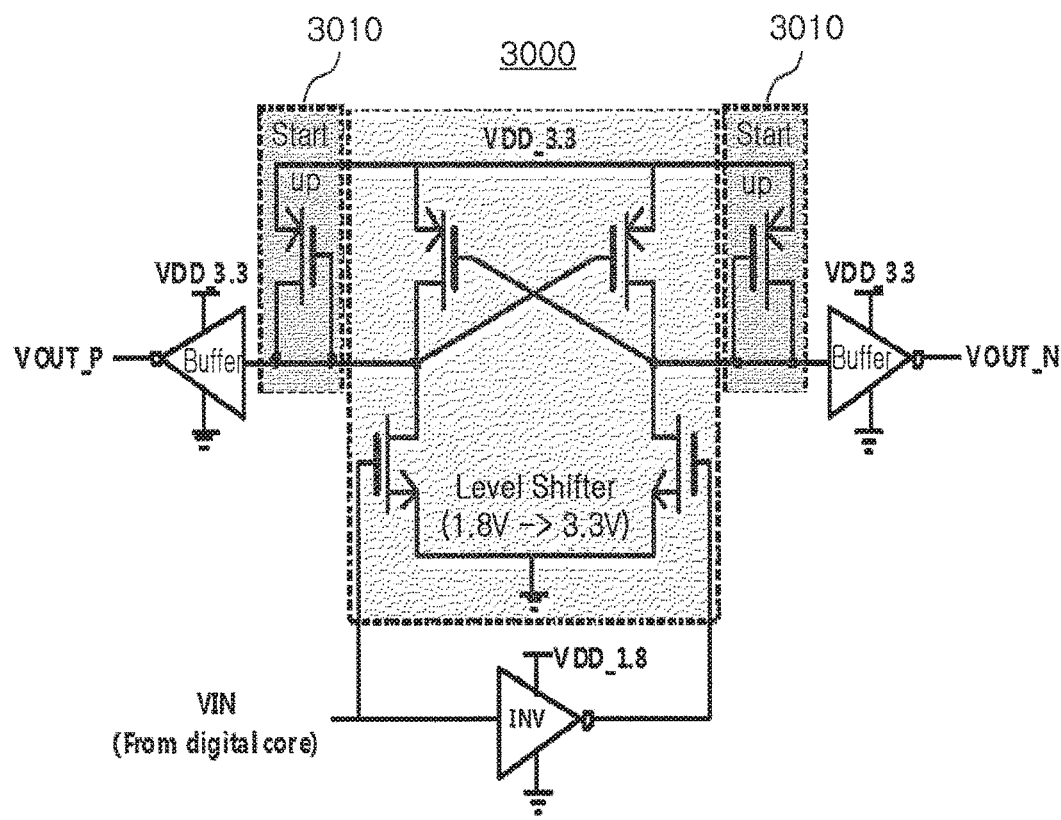
FIG. 30 shows a drive control signal level shifter according to one embodiment of the invention.

FIG. 30 shows a drive control signal level shifter according to one embodiment of the invention. A drive control signal level shifter 3000 may change a control voltage domain in a circuit using 3.3V as VDD in order to cover forward voltage of a laser (e.g., the dual wavelength laser driver 2910) and a LED (e.g., the dual wavelength LED driver 2920). A start-up circuit 3010 may be connected to the drive control signal level shifter 3000 to allocate basic voltage of each node when power is initially turned on.

Figure 31:
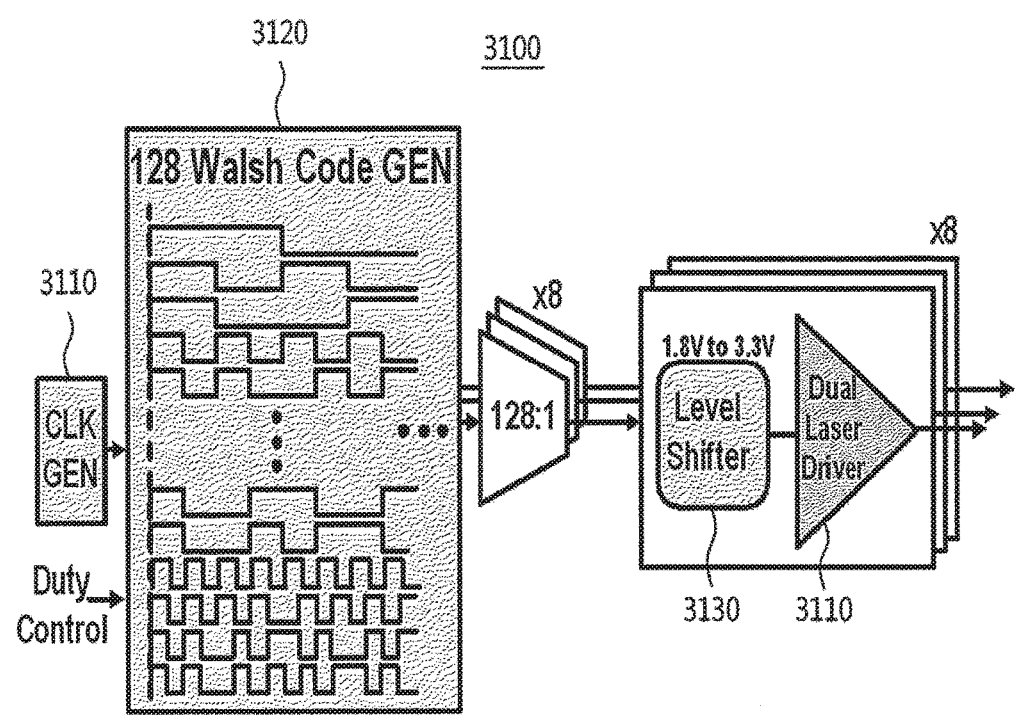
FIG. 31 shows a laser driver using time-divided spread spectrum codes according to one embodiment of the invention.

FIG. 31 shows a laser driver using time-divided spread spectrum codes according to one embodiment of the invention. A dual laser driver 3110 may operate in conjunction with the other components shown in FIG. 31. First, a Walsh code generator (128 Walsh Code GEN) 3120 may generate 128 independent Walsh codes based on a reference clock outputted from a clock generator (CLK GEN) 3130. The Walsh codes to be used may be selected from the 128 Walsh codes as desired by a user, and the selected Walsh codes may be boosted from 1.8V to 3.3V by a level shifter 3130 and then applied to the laser driver 3110 as input signals. A duty control signal may be applied from a microcontroller unit (MCU), and on/off of a laser drive signal may be adjusted in a time domain by the duty control signal.

A method for controlling the optical spectroscopy system according to the present embodiment may comprise the steps of emitting light to a specific region of a subject through a light source in a light transmission unit (e.g., the light transmission unit 411) included in the optical spectroscopy system, wherein total energy is maintained constant by decreasing the time of emitting the light and increasing the intensity of the light, and collecting light coming through the specific region in a light reception unit (e.g., the light reception unit 412) included in the optical spectroscopy system. Here, the light transmission unit may decrease an on/off duty ratio of the light emission by a predetermined ratio using time-divided spread spectrum codes, and increase the intensity of the light by the predetermined ratio. Otherwise, the light transmission unit may decrease unit duration of Walsh codes per unit time by a predetermined ratio using time-divided spread spectrum codes, and increase the intensity of the light by the predetermined ratio. The light source may comprise a dual wavelength laser device and a dual wavelength LED device, and may further comprise a level shifter for changing a control voltage domain of a circuit including the laser device and the LED device. Here, the step of emitting light may comprise the steps of boosting, through the level shifter, a signal corresponding to a code to be used among a predetermined number of mutually independent Walsh codes generated based on a reference clock, and receiving the boosted signal in the laser device as an input signal and adjusting on/off of the input signal using a duty control signal applied from a MCU.

Monitoring Unit

Information obtained by the attachment unit 410 described with reference to FIG. 4 may be processed, visualized, and controlled by the monitoring unit 420. The monitoring unit 420 may be implemented using a device having a display, such as a computer, a notebook, a smart phone, a smart watch, and a tablet PC.

The monitoring unit 420 may include functions for the following (1) to (5).

(1) Optical data of a plurality of wavelengths of each channel separated by firmware (e.g., the firmware 413b of FIG. 4) may be received through wireless communication.

(2) The received data may be processed through digital signal processing. For example, the monitoring unit 420 may process the received data through a low pass filter and a laser temperature drift rejection process.

(3) The processed data may be converted into a concentration change value of oxyhemoglobin and that of deoxyhemoglobin through calculation of the modified Beer-Lambert law.

(4) The concentration change values of oxyhemoglobin and deoxyhemoglobin may be displayed in color on a three-dimensional map.

(5) When the release of a new version of firmware is recognized, the following processes are performed: (a) switching to a firmware update screen of a mobile application (hereinafter, "mobile app") of the monitoring unit 420, (b) entering a firmware update mode of a hardware boot loader, and (c) uploading new firmware.

The release of a new version of firmware is recognized by the following methods (a) and (b).

(a) When the mobile app is executed, it connects to a server and performs user and version check. When the release of a new version of firmware is recognized, it guides the subsequent update.

(b) Whether a new version of firmware is released is notified through a push alarm or other corresponding alarm methods, and the subsequent update is guided.

Figure 32:
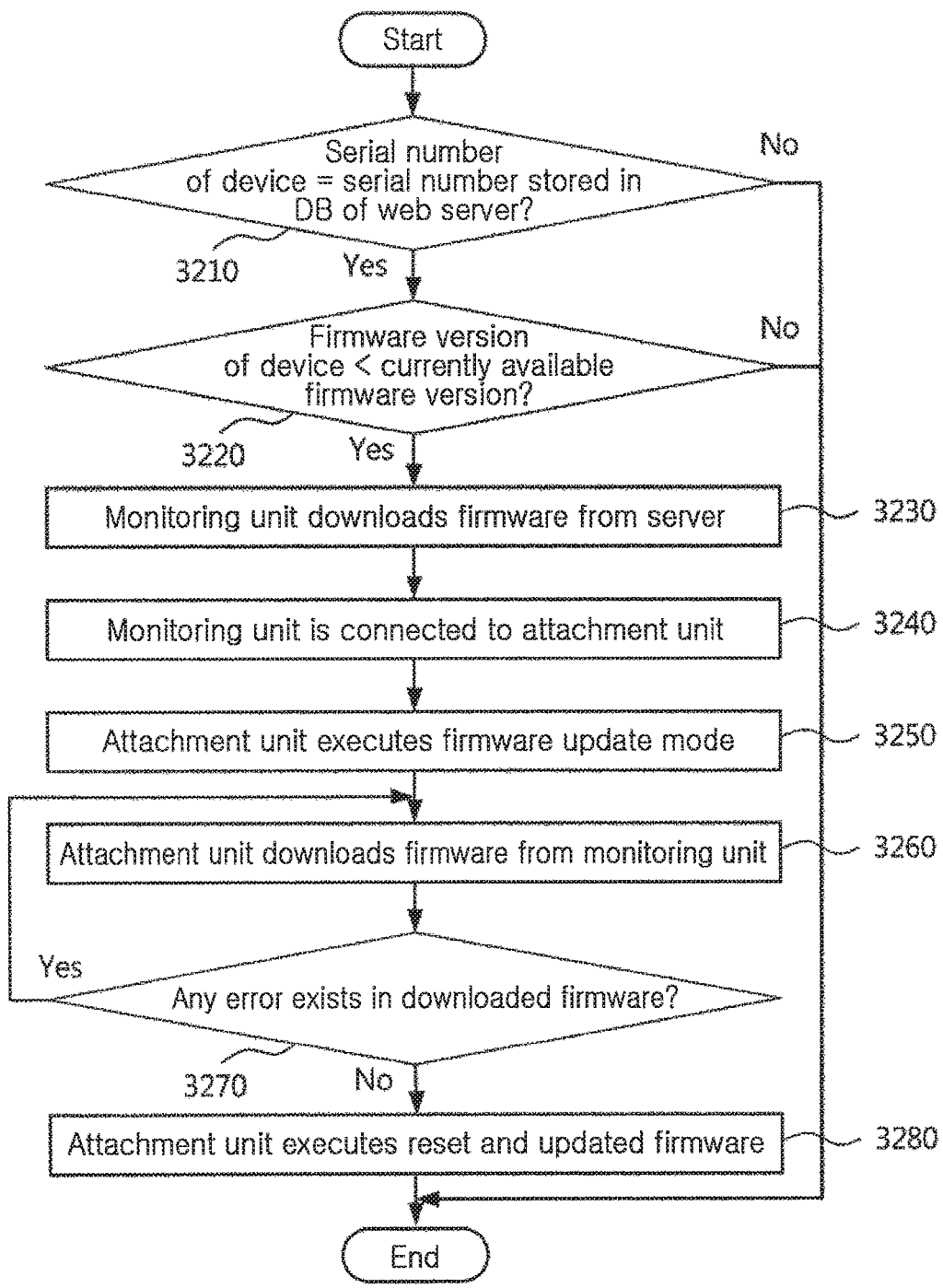
FIG. 32 is a flowchart showing an example of a method for automatic firmware update according to one embodiment of the invention.
Figure 33:
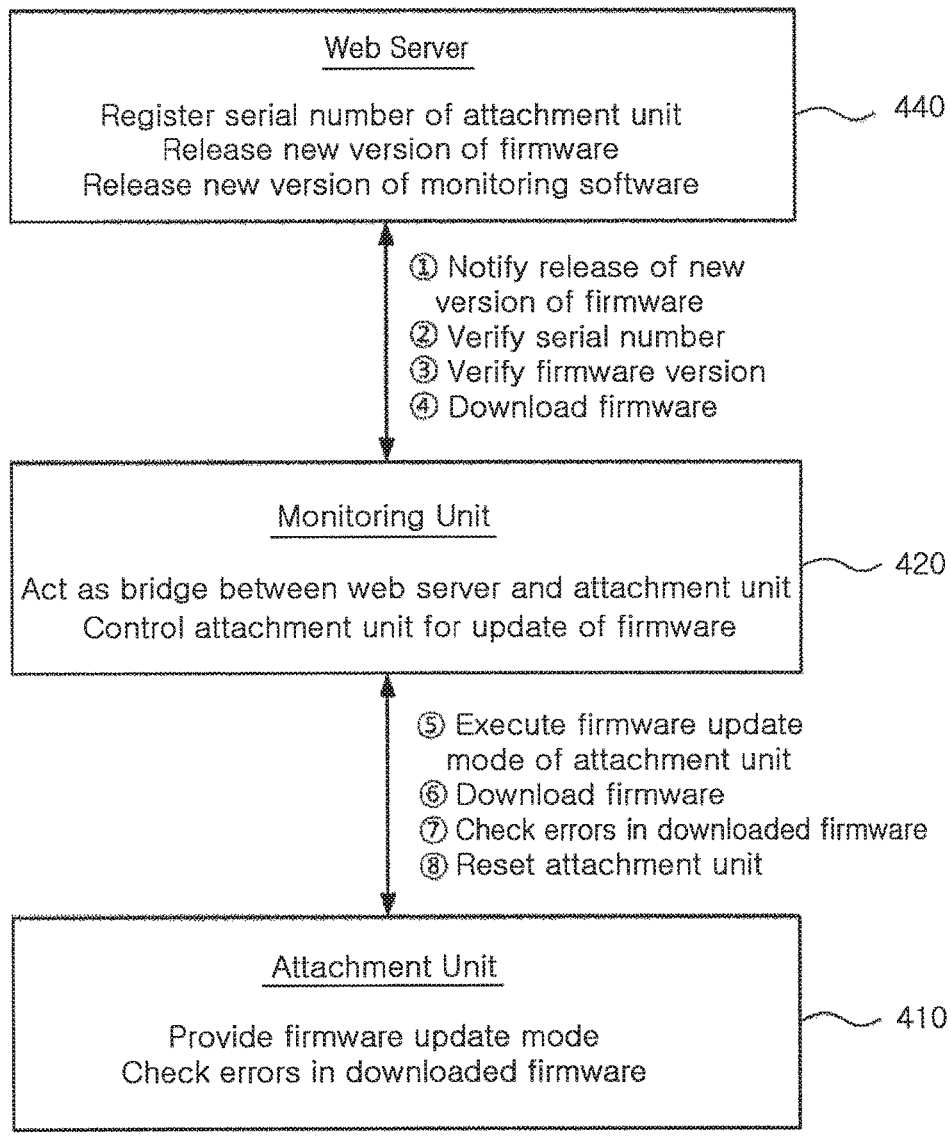
FIG. 33 shows functions for updating firmware according to one embodiment of the invention.

FIG. 32 is a flowchart showing an example of a method for automatic firmware update according to one embodiment of the invention, and FIG. 33 shows functions for updating firmware according to one embodiment of the invention.

In step 3210, the web server 440 may determine whether a serial number of a device is equal to a serial number stored in a database (DB) of the web server 440. To this end, the web server 440 may register the serial number of the device (or the attachment unit). Step 3220 may be performed when the serial number of the device is equal to the registered serial number, and firmware update may be terminated when there is no registered serial number equal to the serial number of the device.

In step 3220, the web server 440 may determine whether a firmware version of the device is lower than the currently available firmware version. The web server 440 may release a new version of firmware and notify the monitoring unit 420 of the release of the new version of firmware.

In step 3230, the monitoring unit 420 may download the firmware from the web server 440. Further, in step 3240, the monitoring unit 420 may be connected to the attachment unit 410. The monitoring unit 420 may act as a bridge between the web server 440 and the attachment unit 410, and may control the attachment unit 410 to update the firmware.

In step 3250, the attachment unit 410 may execute a firmware update mode. Further, in step 3260, the attachment unit 410 may download the firmware from the monitoring unit 420.

In step 3270, the attachment unit 410 may determine whether any error exists in the downloaded firmware. Step 3260 may be performed again when any error exists, and step 3280 may be performed when no error exists. As above, the attachment unit 410 may include a function of checking errors in the downloaded firmware.

In step 3280, the attachment unit 410 may execute the reset and updated firmware.

Big Data Analysis

Figure 34:
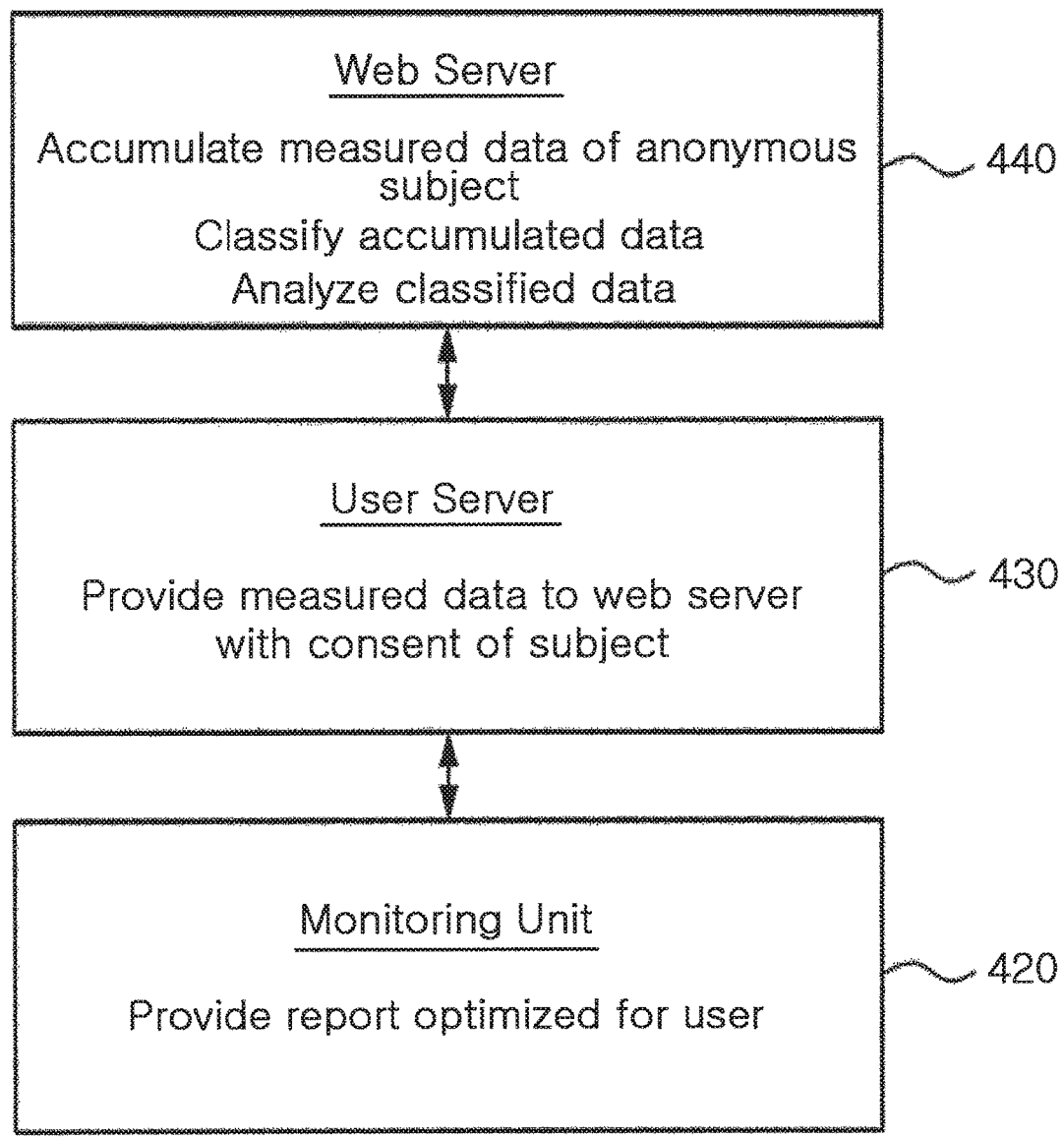
FIG. 34 shows functions for processing big data according to one embodiment of the invention.

FIG. 34 shows functions for processing big data according to one embodiment of the invention. The web server 440 may collect data on an anonymous subject who has consented from the user server 430 and perform big data analysis as follows:

(1) The user server 430 may inquire of a subject whether or not to provide measured data to the web server 440. For example, the user server 430 may provide the measured data to the web server 440 with the consent of the anonymous subject.

(2) When the anonymous subject consents to information provision in the user server 430, the web server 440 may anonymously collect the measured data from the user server 430.

(3) The web server 440 may accumulate the measured data of the anonymous subject, classify the accumulated data, and analyze the classified data.

(4) The web server 440 may provide personalized results of big data analysis on the personal measurement data to the monitoring unit 420 through the user server 430, only for the subject who has consented to the information provision, and the monitoring unit 420 may provide a report optimized for the user (e.g., display it on a screen).

Through the application of the big data analysis, it is possible to detect a symptom early from the measurement results of the user by comparing the results obtained from a conventional apparatus or an optical spectroscopy system regarding a specific disease such as a stroke.

In addition, information on various diseases that has not been recognized before may be accumulated based on measurement results in a similar environment, and the accumulated information may be used to analyze a wider range of data and detect a symptom of a disease.

Further, through the accumulation and analysis of personal measurement data, it is possible to continuously monitor the changes in patients who have a high likelihood of recurrence and need continuous management, so that risk factors may be discovered in advance. In other words, it is possible to continuously accumulate personal measurement data to construct personal big data, and to compare and analyze the big data to discover any risk factor in the current measurement result of the user or provide a report optimized for the user regarding any recognized changes.

Furthermore, for the same reasons as the above, it is possible to accumulate and recognize personal measurement data when it is necessary to recognize the effects of gradual changes (e.g., during rehabilitation), and to develop a personal rehabilitation program.

As described above, according to the embodiments of the invention, it is possible to provide a mobile and expandable firmware-based optical spectroscopy system and a method for controlling the same.

Further, it is possible to use a pipeline-structured matched filter to implement a matched filter structure for the same time as a bit period of input Walsh codes, and minimize current leakage and nonlinear effects occurring in a switching circuit.

Further, it is possible to use time-divided spread spectrum codes (TDSSC) to reduce duration of 1 of Walsh codes per unit time and inject more intense light, thereby increasing the intensity of the light with the same total energy.

Further, it is possible to modulate light emitted from a plurality of light sources using Walsh codes and emit the modulated light, and detect light coming through a specific region and demodulate the detected light using the Walsh codes, thereby distinguishing the light source that has emitted the light.

Further, it is possible to accumulate input signals using a reference clock used for light emission as a sampling clock, thereby minimizing white Gaussian noise without additional circuitry such as an additional phase locked loop (PLL).

Further, it is possible to process, visualize, and control data in a monitoring device, and guide firmware update according to the release of a new version of firmware included in an attachment device such as a headset.

Further, it is possible to collect, manage, and analyze data measured through a web server and provide personalized results through a monitoring device.

The above-described devices (i.e., the optical spectroscopy system 400, the attachment unit 410, the monitoring unit 420, the user server 430, and the web server 440) may be implemented with hardware components, software components, and/or a combination of hardware and software components. For example, the devices and components described in the embodiments may be implemented using one or more general or special purpose computers, such as a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications running on the operating system. Further, the processing device may also access, store, manipulate, process, and generate data in response to the execution of the software. For ease of understanding, the processing device may be described as being used singly, but those skilled in the art will appreciate that the processing device may include a plurality of processing elements and/or a plurality of types of processing elements. For example, the processing device may comprise a plurality of processors or one processor and one controller. Further, other processing configurations such as a parallel processor are also possible.

The software may comprise computer programs, codes, instructions, or a combination of one or more of the foregoing, and may configure the processing device to operate as desired or instruct the processing device independently or collectively. Software and/or data may be permanently or temporarily embodied in any type of machine, component, physical device, virtual equipment, computer storage medium or device, or a transmitted signal wave, so that the software and/or data may be interpreted by the processing device or may provide instructions or data to the processing device. The software may be distributed over networked computer systems, and may be stored or executed in a distributed manner. The software and data may be stored on one or more computer-readable recording media.

The method according to the embodiments of the invention may be implemented in the form of program instructions that can be executed by various computer means, and may be stored on a computer-readable recording medium. The computer-readable recording medium may include program instructions, data files, data structures and the like, separately or in combination. The program instructions stored on the medium may be specially designed and configured for the embodiments, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be configured to operate as one or more software modules to perform the processes of the embodiments, and vice versa.

Although the embodiments have been described in terms of the limited embodiments and drawings, those skilled in the art can make various modifications and changes from the above description. For example, appropriate results can be achieved even if the described techniques are performed in a different order than the described methods, and/or the components of the described systems, structures, devices, circuits, and the like are coupled or combined in a different form than the described methods, or changed to or replaced with other components or equivalents.

Therefore, other implementations, other embodiments, and equivalents to the appended claims also fall within the scope of the following claims.

What is claimed is:

1. An optical spectroscopy system, comprising:
    a light transmission unit for emitting light to a specific region of a subject through a light source, such that total energy is maintained constant by decreasing time of emitting the light and increasing an intensity of the light; and
    a light reception unit for collecting light coming through the specific region,
    wherein the light reception unit uses a reference clock used for light emission as a sampling clock.

2. The optical spectroscopy system of claim 1, wherein the light transmission unit decreases an on/off duty ratio of the light emission by a predetermined ratio, and increases the intensity of the light by the predetermined ratio.

3. The optical spectroscopy system of claim 1, wherein the light source comprises a dual wavelength laser device and a dual wavelength light emitting diode (LED) device, and further comprises a level shifter for changing a control voltage domain of a circuit including the laser device and the LED device.

4. The optical spectroscopy system of claim 3, wherein when initial power is supplied, a start-up circuit for allocating basic voltage to devices included in the level shifter is connected to both ends of the level shifter.

5. The optical spectroscopy system of claim 3, wherein a signal is boosted through the level shifter, the signal corresponding to a code to be used among a predetermined number of mutually independent orthogonal codes generated based on a reference clock, and the boosted signal is received in the laser device as an input signal, so that on/off of the input signal is adjusted using a duty control signal applied from a microcontroller unit (MCU).

6. A method for controlling an optical spectroscopy system, comprising the steps of:
    by a light transmission unit included in the optical spectroscopy system, emitting light to a specific region of a subject through a light source, such that total energy is maintained constant by decreasing time of emitting the light and increasing an intensity of the light; and
    by a light reception unit included in the optical spectroscopy system, collecting light coming through the specific region,
    wherein the light reception unit uses a reference clock used for light emission as a sampling clock.

7. The method of claim 6, wherein in the step of emitting light, an on/off duty ratio of the light emission is decreased by a predetermined, and the intensity of the light is increased by the predetermined ratio.

8. The method of claim 6, wherein the light source comprises a dual wavelength laser device and a dual wavelength light emitting diode (LED) device, and further comprises a level shifter for changing a control voltage domain of a circuit including the laser device and the LED device.

9. The method of claim 8, wherein the step of emitting light comprises the steps of:
- boosting, through the level shifter, a signal corresponding to a code to be used among a predetermined number of mutually independent orthogonal codes generated based on a reference clock; and
- receiving the boosted signal in the laser device as an input signal, and adjusting on/off of the input signal using a duty control signal applied from a microcontroller unit (MCU).

* * * * *

UNITED STATES PATENT AND TRADEMARK OFFICE
CERTIFICATE OF CORRECTION

PATENT NO. : 10,254,165 B2
APPLICATION NO. : 15/523110
DATED : April 9, 2019
INVENTOR(S) : Hyeon Min Bae et al.

It is certified that error appears in the above-identified patent and that said Letters Patent is hereby corrected as shown below:

In the Claims

In Column 22 Line 66, in Claim 7, after "by a predetermined", add "ratio".

Signed and Sealed this
Eighteenth Day of June, 2019

Andrei Iancu
*Director of the United States Patent and Trademark Office*